US010174387B2

(12) United States Patent
Bai et al.

(10) Patent No.: US 10,174,387 B2
(45) Date of Patent: Jan. 8, 2019

(54) SOYBEAN MARKERS LINKED TO PHYTOPHTHORA RESISTANCE

(71) Applicant: Dow AgroSciences LLC, Indianapolis, IN (US)

(72) Inventors: Yonghe Bai, Westfield, IN (US); Fang Lu, Westfield, IN (US); Tyler Mansfield, Indianapolis, IN (US); Jenelle Meyer, Zionsville, IN (US); Robert E. Moore, Gibson City, IL (US); Bradley Hedges, Kingsville (CA); William M. Campbell, Clinton, WI (US); Julu Manandhar, Champaign, IL (US); Jan E. Backlund, Indianapolis, IN (US); David H. Meyer, Indianapolis, IN (US); Siva P. Kumpatla, Carmel, IN (US); Raghav Ram, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 303 days.

(21) Appl. No.: 14/204,284

(22) Filed: Mar. 11, 2014

(65) Prior Publication Data
US 2014/0283197 A1 Sep. 18, 2014

Related U.S. Application Data

(60) Provisional application No. 61/777,575, filed on Mar. 12, 2013.

(51) Int. Cl.
*A01H 5/10* (2018.01)
*C12Q 1/6895* (2018.01)
*C12N 15/82* (2006.01)
*A01H 1/04* (2006.01)

(52) U.S. Cl.
CPC ............ *C12Q 1/6895* (2013.01); *A01H 1/04* (2013.01); *C12N 15/8279* (2013.01); *C12Q 2600/13* (2013.01)

(58) Field of Classification Search
None
See application file for complete search history.

(56) References Cited

U.S. PATENT DOCUMENTS

| 7,256,323 | B1 | 8/2007 | Bhattacharyya | |
| 7,696,410 | B1* | 4/2010 | Bhattacharyya | ... C12N 15/8282 435/320.1 |
| 2006/0247197 | A1 | 11/2006 | Van De Craen et al. | |
| 2007/0083945 | A1* | 4/2007 | Byrum ................. | C07K 14/415 800/278 |
| 2008/0263720 | A1 | 10/2008 | Behm et al. | |
| 2010/0122375 | A1 | 5/2010 | Bhattacharyya et al. | |

FOREIGN PATENT DOCUMENTS

| CA | 2269215 A1 | 10/1999 |
| CA | 2627079 | 1/2008 |
| CN | 101372710 | 2/2009 |
| WO | WO2006017833 A2 | 2/2006 |
| WO | WO2006070227 A2 | 7/2006 |
| WO | WO2008054546 A2 | 5/2008 |

OTHER PUBLICATIONS

Batley and Edwards, 2007, In; Association Mapping in Plants, pp. 95-102.*
Sugimoto et al., 2006, Breeding Science 61: 511-522.*
Burnham, K. D., A. E. Dorrance, T. T. Vantoai and S. K. St. Martin, 2003 Quantitative trait loci for partial resistance to in soybean. Crop Sci. 43: 1610-1617.
Ferro, C. R., C. B. Hill, M. R. Miles and G. L. Hartman, 2006 Evaluation of soybean cultivars with the gene for partial resistance or field tolerance to Phytophthora sojae. Crop Sci. 46: 2427-2436.
Gao, H., N. N. Narayanan, L. Ellison and M. K. Bhattacharyya, 2005 Two classes of highly similar coiled coil-nucleotide Binding-leucine rich repeat genes isolated from the Rps1-k locus encode Phytophthora resistance in soybean. Molecular Plant-Microbe Interactions 18: 1035-1045.
Li, X., Y. Han, W. Teng, S. Zhang, K. Yu et al., Pyramided QTL underlying tolerance to Phytophthora root rot in mega-environments from soybean cultivars 'Conrad' and 'Hefeng 25'. TAG Theoretical and Applied Genetics 121: 651-658.
Ranathunge, K., R. H. Thomas, X. Fang, C. A. Peterson, M. Gijzen et al., 2008 Soybean root suberin and partial resistance to root rot caused by Phytophthora sojae. Phytopathology 98: 1179-1189.
Slaminko, T., C. R. Bowen and G. L. Hartman, 2010 Multi-year evaluation of commercial soybean cultivars for resistance to Phytophthora sojae. Plant Disease 94: 368-371.
Tucker, D. M., M. A. Saghai Maroof, S. Mideros, J. A. Skoneczka, D. A. Nabati et al., 2010 Mapping quantitative trait loci for partial resistance to Phytophthora sojae in a soybean interspecific cross. Crop Sci. 50: 628-635.
Wrather, J. A., and S. R. Koenning, 2006 Estimates of disease effects on soybean yields in the United States 2003 to 2005. J Nematol 38: 173-180.
Burnham, K. D., A. E. Dorrance, D. M. Francis, R. J. Fioritto and S. K. St. Martin, 2003 Rps8, A new locus in soybean for resistance to Phytophthora sojae. Crop Science 43: 101-105.
Dou, D., S. D. Kale, T. Liu, Q. Tang, X. Wang et al., 2010 Different domains of Phytophthora sojae effector Avr4/6 Are recognized by soybean resistance genes Rps4 and Rps6. Mol Plant Microbe Interact 23: 425-435.

(Continued)

Primary Examiner — Amjad Abraham
Assistant Examiner — Bratislav Stankovic
(74) *Attorney, Agent, or Firm* — Magleby Cataxinos & Greenwood

(57) ABSTRACT

This disclosure concerns compositions and methods for identifying the *phytophthora* resistant phenotype in soybean. In some embodiments, the disclosure concerns methods for performing marker-assisted breeding and selection of plants carrying one or more determinants of *phytophthora* resistance in soybean. In some embodiments, the disclosure concerns methods for detecting *phytophthora* resistance in soybean via the use of an amplification reaction.

5 Claims, 3 Drawing Sheets

Specification includes a Sequence Listing.

(56) References Cited

OTHER PUBLICATIONS

Gao, H., and M. K. Bhattacharyya, 2008 the soybean-Phytophthora resistance locus Rps1-k encompasses coiled coil-nucleotide binding-leucine rich repeat-like genes and repetitive sequences. BMC Plant Biol 8: 29.
Gardner, M. E., T. Hymowitz, S. J. Xu and G. L. Hartman, 2001 Physical map location of the Rps1-k allele in soybean. Crop Science 41: 1435-1438.
Kasuga, T., S. S. Salimath, J. Shi, M. Gijzen, R. I. Buzzell et al., 1997 High resolution genetic and physical mapping of molecular markers linked to the Phytophthora resistance gene Rps1-k in soybean. Mol Plant-Microbe Interact 10: 1035-1044.
Polzin, K. M., L. L. Lorenzen, T. C. Olson and R. C. Shoemaker, 1994 an unusual polymorphic locus useful for tagging Rps1 resistance alleles in soybean. Theor Appl Genet 89: 226-232.

* cited by examiner

SEQUENCE LISTING

```
<160> NUMBER OF SEQ ID NOS: 159

<210> SEQ ID NO 1
<211> LENGTH: 21
<212> TYPE: DNA
<213> ORGANISM: Glycine max

<400> SEQUENCE: 1
tcacatgttc ragttcctac t                                       21

<210> SEQ ID NO 2
<211> LENGTH: 21
<212> TYPE: DNA
<213> ORGANISM: Glycine max

<400> SEQUENCE: 2
tactctcagc ygacatgcga a                                       21

<210> SEQ ID NO 3
<211> LENGTH: 21
<212> TYPE: DNA
<213> ORGANISM: Glycine max

<400> SEQUENCE: 3
ttcacaatta rcatgcaaca t                                       21

<210> SEQ ID NO 4
<211> LENGTH: 21
<212> TYPE: DNA
<213> ORGANISM: Glycine max
```

```
<400> SEQUENCE: 4
tttttttctc yatttataat t                                              21

<210> SEQ ID NO 5
<211> LENGTH: 21
<212> TYPE: DNA
<213> ORGANISM: Glycine max
<220> FEATURE:
<221> NAME/KEY: misc_feature
<222> LOCATION: (5)..(5)
<223> OTHER INFORMATION: miscellaneous SNP; not targeted SNP
<220> FEATURE:
<221> NAME/KEY: misc_feature
<222> LOCATION: (7)..(7)
<223> OTHER INFORMATION: miscellaneous SNP; not targeted SNP

<400> SEQUENCE: 5
ggcawckggg mttgaggcaa g                                              21

<210> SEQ ID NO 6
<211> LENGTH: 21
<212> TYPE: DNA
<213> ORGANISM: Glycine max
<220> FEATURE:
<221> NAME/KEY: misc_feature
<222> LOCATION: (16)..(16)
<223> OTHER INFORMATION: miscellaneous SNP; not targeted SNP
<220> FEATURE:
<221> NAME/KEY: misc_feature
<222> LOCATION: (18)..(18)
<223> OTHER INFORMATION: miscellaneous SNP; not targeted SNP

<400> SEQUENCE: 6
agtgcttgtt yggcawckgg g                                              21

<210> SEQ ID NO 7
<211> LENGTH: 21
<212> TYPE: DNA
<213> ORGANISM: Glycine max

<400> SEQUENCE: 7
cctataataa yatgcatata g                                              21

<210> SEQ ID NO 8
<211> LENGTH: 21
<212> TYPE: DNA
<213> ORGANISM: Glycine max

<400> SEQUENCE: 8
tcacaatgag rctgagcaat g                                              21

<210> SEQ ID NO 9
<211> LENGTH: 21
<212> TYPE: DNA
<213> ORGANISM: Glycine max

<400> SEQUENCE: 9
ggtacaccca rcataacttg c                                              21

<210> SEQ ID NO 10
<211> LENGTH: 21
<212> TYPE: DNA
<213> ORGANISM: Glycine max

<400> SEQUENCE: 10
taatgttcag rttttttctg c                                              21
```

```
<210> SEQ ID NO 11
<211> LENGTH: 21
<212> TYPE: DNA
<213> ORGANISM: Glycine max

<400> SEQUENCE: 11
tacatttgca ygcaaatgat t                                              21

<210> SEQ ID NO 12
<211> LENGTH: 21
<212> TYPE: DNA
<213> ORGANISM: Glycine max

<400> SEQUENCE: 12
catttgccga ygcactaaat a                                              21

<210> SEQ ID NO 13
<211> LENGTH: 21
<212> TYPE: DNA
<213> ORGANISM: Glycine max

<400> SEQUENCE: 13
tttttaagga rcagcttgag a                                              21

<210> SEQ ID NO 14
<211> LENGTH: 21
<212> TYPE: DNA
<213> ORGANISM: Glycine max

<400> SEQUENCE: 14
catgaatcct satgttgctc a                                              21

<210> SEQ ID NO 15
<211> LENGTH: 21
<212> TYPE: DNA
<213> ORGANISM: Glycine max

<400> SEQUENCE: 15
caagaatgcc wtcaacgcca t                                              21

<210> SEQ ID NO 16
<211> LENGTH: 21
<212> TYPE: DNA
<213> ORGANISM: Glycine max

<400> SEQUENCE: 16
ttgactgatg rtaatgagaa a                                              21

<210> SEQ ID NO 17
<211> LENGTH: 21
<212> TYPE: DNA
<213> ORGANISM: Glycine max

<400> SEQUENCE: 17
ctttcttgta racgatgcaa c                                              21

<210> SEQ ID NO 18
<211> LENGTH: 21
<212> TYPE: DNA
<213> ORGANISM: Glycine max

<400> SEQUENCE: 18
tattccccaa rtaatagcta a                                              21
```

```
<210> SEQ ID NO 19
<211> LENGTH: 21
<212> TYPE: DNA
<213> ORGANISM: Glycine max

<400> SEQUENCE: 19
gattataaat wtaaaaggt t                                              21

<210> SEQ ID NO 20
<211> LENGTH: 21
<212> TYPE: DNA
<213> ORGANISM: Glycine max

<400> SEQUENCE: 20
tgatcatata yagtaaaaca a                                             21

<210> SEQ ID NO 21
<211> LENGTH: 21
<212> TYPE: DNA
<213> ORGANISM: Glycine max

<400> SEQUENCE: 21
tttgggacta stctaggaaa c                                             21

<210> SEQ ID NO 22
<211> LENGTH: 21
<212> TYPE: DNA
<213> ORGANISM: Glycine max

<400> SEQUENCE: 22
tttgagaaaa rtaagcatgc a                                             21

<210> SEQ ID NO 23
<211> LENGTH: 21
<212> TYPE: DNA
<213> ORGANISM: Glycine max

<400> SEQUENCE: 23
tgcacccgga kgagtgttag a                                             21

<210> SEQ ID NO 24
<211> LENGTH: 21
<212> TYPE: DNA
<213> ORGANISM: Glycine max
<220> FEATURE:
<221> NAME/KEY: misc_feature
<222> LOCATION: (5)..(5)
<223> OTHER INFORMATION: where n is a, t, c or g

<400> SEQUENCE: 24
aactnaaatg rgggagaaaa g                                             21

<210> SEQ ID NO 25
<211> LENGTH: 21
<212> TYPE: DNA
<213> ORGANISM: Glycine max

<400> SEQUENCE: 25
agtaacaatg ycagaagtct a                                             21

<210> SEQ ID NO 26
<211> LENGTH: 21
<212> TYPE: DNA
<213> ORGANISM: Glycine max
```

```
<400> SEQUENCE: 26
aatttgcaga yggaaccaac a                                        21

<210> SEQ ID NO 27
<211> LENGTH: 21
<212> TYPE: DNA
<213> ORGANISM: Glycine max

<400> SEQUENCE: 27
atctgcattt ycctatcagg a                                        21

<210> SEQ ID NO 28
<211> LENGTH: 21
<212> TYPE: DNA
<213> ORGANISM: Glycine max

<400> SEQUENCE: 28
gtgagcagca scatcagaaa g                                        21

<210> SEQ ID NO 29
<211> LENGTH: 21
<212> TYPE: DNA
<213> ORGANISM: Glycine max

<400> SEQUENCE: 29
actacatgtt wagacacctt c                                        21

<210> SEQ ID NO 30
<211> LENGTH: 21
<212> TYPE: DNA
<213> ORGANISM: Glycine max

<400> SEQUENCE: 30
tgaacgtgta wgataggcac a                                        21

<210> SEQ ID NO 31
<211> LENGTH: 21
<212> TYPE: DNA
<213> ORGANISM: Glycine max

<400> SEQUENCE: 31
tatgtgtata ytgagttttg a                                        21

<210> SEQ ID NO 32
<211> LENGTH: 21
<212> TYPE: DNA
<213> ORGANISM: Glycine max
<220> FEATURE:
<221> NAME/KEY: misc_feature
<222> LOCATION: (12)..(12)
<223> OTHER INFORMATION: where n is a, t, c or g
<220> FEATURE:
<221> NAME/KEY: misc_feature
<222> LOCATION: (15)..(15)
<223> OTHER INFORMATION: where n is a, t, c or g

<400> SEQUENCE: 32
tctcaaatat ynacnattga t                                        21

<210> SEQ ID NO 33
<211> LENGTH: 21
<212> TYPE: DNA
<213> ORGANISM: Glycine max
```

```
<220> FEATURE:
<221> NAME/KEY: misc_feature
<222> LOCATION: (12)..(12)
<223> OTHER INFORMATION: where n is a, t, c or g

<400> SEQUENCE: 33
tttgattcct wnaaaaaaaa t                                              21

<210> SEQ ID NO 34
<211> LENGTH: 21
<212> TYPE: DNA
<213> ORGANISM: Glycine max
<220> FEATURE:
<221> NAME/KEY: misc_feature
<222> LOCATION: (2)..(2)
<223> OTHER INFORMATION: miscellaneous SNP; not targeted SNP

<400> SEQUENCE: 34
twtatttatg yattcactag t                                              21

<210> SEQ ID NO 35
<211> LENGTH: 21
<212> TYPE: DNA
<213> ORGANISM: Glycine max

<400> SEQUENCE: 35
cttgcattgc mtttcctcat t                                              21

<210> SEQ ID NO 36
<211> LENGTH: 21
<212> TYPE: DNA
<213> ORGANISM: Glycine max

<400> SEQUENCE: 36
aattggaaat ygctgccaaa g                                              21

<210> SEQ ID NO 37
<211> LENGTH: 21
<212> TYPE: DNA
<213> ORGANISM: Glycine max

<400> SEQUENCE: 37
gaagcatgca wagaagatat g                                              21

<210> SEQ ID NO 38
<211> LENGTH: 21
<212> TYPE: DNA
<213> ORGANISM: Glycine max

<400> SEQUENCE: 38
aaaggaattg ycatacttct t                                              21

<210> SEQ ID NO 39
<211> LENGTH: 21
<212> TYPE: DNA
<213> ORGANISM: Glycine max

<400> SEQUENCE: 39
tctttcaaca ktacaccgtc t                                              21

<210> SEQ ID NO 40
<211> LENGTH: 21
<212> TYPE: DNA
<213> ORGANISM: Glycine max
```

```
<400> SEQUENCE: 40
ttaccctagt mtaaatctgt a                                              21

<210> SEQ ID NO 41
<211> LENGTH: 21
<212> TYPE: DNA
<213> ORGANISM: Glycine max

<400> SEQUENCE: 41
aaccatattt waaaacgtct t                                              21

<210> SEQ ID NO 42
<211> LENGTH: 21
<212> TYPE: DNA
<213> ORGANISM: Glycine max

<400> SEQUENCE: 42
ggatatttga yttggtcgag t                                              21

<210> SEQ ID NO 43
<211> LENGTH: 21
<212> TYPE: DNA
<213> ORGANISM: Glycine max

<400> SEQUENCE: 43
aaatattatg watgtttcaa t                                              21

<210> SEQ ID NO 44
<211> LENGTH: 21
<212> TYPE: DNA
<213> ORGANISM: Glycine max

<400> SEQUENCE: 44
tcaaagttgt maaatctatg g                                              21

<210> SEQ ID NO 45
<211> LENGTH: 21
<212> TYPE: DNA
<213> ORGANISM: Glycine max

<400> SEQUENCE: 45
tagttgagaa wgcgatttca t                                              21

<210> SEQ ID NO 46
<211> LENGTH: 21
<212> TYPE: DNA
<213> ORGANISM: Glycine max

<400> SEQUENCE: 46
attcctttgt yctaaatttg a                                              21

<210> SEQ ID NO 47
<211> LENGTH: 21
<212> TYPE: DNA
<213> ORGANISM: Glycine max

<400> SEQUENCE: 47
ccactagtta rctagtagta t                                              21

<210> SEQ ID NO 48
<211> LENGTH: 21
<212> TYPE: DNA
<213> ORGANISM: Glycine max
```

```
<400> SEQUENCE: 48
ttgcagaaag waagtaagac t                                              21

<210> SEQ ID NO 49
<211> LENGTH: 21
<212> TYPE: DNA
<213> ORGANISM: Glycine max

<400> SEQUENCE: 49
aaaacctctc rggtataaac t                                              21

<210> SEQ ID NO 50
<211> LENGTH: 21
<212> TYPE: DNA
<213> ORGANISM: Glycine max

<400> SEQUENCE: 50
cttggctttt yaatgtgttt t                                              21

<210> SEQ ID NO 51
<211> LENGTH: 21
<212> TYPE: DNA
<213> ORGANISM: Glycine max

<400> SEQUENCE: 51
catcacggtg matgtgatcc c                                              21

<210> SEQ ID NO 52
<211> LENGTH: 21
<212> TYPE: DNA
<213> ORGANISM: Glycine max

<400> SEQUENCE: 52
aaaatattaa wgaaacaaca c                                              21

<210> SEQ ID NO 53
<211> LENGTH: 21
<212> TYPE: DNA
<213> ORGANISM: Glycine max

<400> SEQUENCE: 53
gcaatgtcct ratggtccag a                                              21

<210> SEQ ID NO 54
<211> LENGTH: 21
<212> TYPE: DNA
<213> ORGANISM: Glycine max

<400> SEQUENCE: 54
acgcgttaag ycgcatggtg c                                              21

<210> SEQ ID NO 55
<211> LENGTH: 21
<212> TYPE: DNA
<213> ORGANISM: Glycine max

<400> SEQUENCE: 55
gagccacttt wtatatatat a                                              21

<210> SEQ ID NO 56
<211> LENGTH: 21
<212> TYPE: DNA
<213> ORGANISM: Glycine max
```

```
<400> SEQUENCE: 56 tttttaaat ygattatgca t                                        21

<210> SEQ ID NO 57
<211> LENGTH: 21
<212> TYPE: DNA
<213> ORGANISM: Glycine max

<400> SEQUENCE: 57
ttatattcat ktattgtatt a                                       21

<210> SEQ ID NO 58
<211> LENGTH: 21
<212> TYPE: DNA
<213> ORGANISM: Glycine max

<400> SEQUENCE: 58
ggagtgtgaa rttgaatgga t                                       21

<210> SEQ ID NO 59
<211> LENGTH: 21
<212> TYPE: DNA
<213> ORGANISM: Glycine max

<400> SEQUENCE: 59
tccataattt kgtggttatg a                                       21

<210> SEQ ID NO 60
<211> LENGTH: 21
<212> TYPE: DNA
<213> ORGANISM: Glycine max

<400> SEQUENCE: 60
aatgagatac yagctgcttc c                                       21

<210> SEQ ID NO 61
<211> LENGTH: 21
<212> TYPE: DNA
<213> ORGANISM: Glycine max

<400> SEQUENCE: 61
ccaaataggc matactaata g                                       21

<210> SEQ ID NO 62
<211> LENGTH: 21
<212> TYPE: DNA
<213> ORGANISM: Glycine max

<400> SEQUENCE: 62
cagcttttcc yttaaaaaaa t                                       21

<210> SEQ ID NO 63
<211> LENGTH: 21
<212> TYPE: DNA
<213> ORGANISM: Glycine max

<400> SEQUENCE: 63
ccaaaatctt ytgatgggaa g                                       21

<210> SEQ ID NO 64
<211> LENGTH: 21
<212> TYPE: DNA
<213> ORGANISM: Glycine max
```

```
<400> SEQUENCE: 64
aagaaaacga rttgcattag g                                         21

<210> SEQ ID NO 65
<211> LENGTH: 21
<212> TYPE: DNA
<213> ORGANISM: Glycine max

<400> SEQUENCE: 65
ggctgagttg yttattataa g                                         21

<210> SEQ ID NO 66
<211> LENGTH: 21
<212> TYPE: DNA
<213> ORGANISM: Glycine max

<400> SEQUENCE: 66
ttcacaataa yattcttctt c                                         21

<210> SEQ ID NO 67
<211> LENGTH: 21
<212> TYPE: DNA
<213> ORGANISM: Glycine max

<400> SEQUENCE: 67
gaatcgggag ytatgggaat g                                         21

<210> SEQ ID NO 68
<211> LENGTH: 21
<212> TYPE: DNA
<213> ORGANISM: Glycine max

<400> SEQUENCE: 68
cattattttc rtttatcgga t                                         21

<210> SEQ ID NO 69
<211> LENGTH: 21
<212> TYPE: DNA
<213> ORGANISM: Glycine max

<400> SEQUENCE: 69
ggcagaagca kaggatttca c                                         21

<210> SEQ ID NO 70
<211> LENGTH: 21
<212> TYPE: DNA
<213> ORGANISM: Glycine max

<400> SEQUENCE: 70
ccgaaaccgt ygcaacagaa c                                         21

<210> SEQ ID NO 71
<211> LENGTH: 21
<212> TYPE: DNA
<213> ORGANISM: Glycine max

<400> SEQUENCE: 71
tttagatctg rtgctaacta t                                         21

<210> SEQ ID NO 72
<211> LENGTH: 21
<212> TYPE: DNA
<213> ORGANISM: Glycine max
```

```
<400> SEQUENCE: 72
ttcaacaatg rcattgagtg t                                              21

<210> SEQ ID NO 73
<211> LENGTH: 21
<212> TYPE: DNA
<213> ORGANISM: Glycine max

<400> SEQUENCE: 73
gaaaaaaata rctgatgtgt t                                              21

<210> SEQ ID NO 74
<211> LENGTH: 21
<212> TYPE: DNA
<213> ORGANISM: Glycine max

<400> SEQUENCE: 74
gcaaagcaat kacacattct g                                              21

<210> SEQ ID NO 75
<211> LENGTH: 21
<212> TYPE: DNA
<213> ORGANISM: Glycine max

<400> SEQUENCE: 75
tgtaacaata kcaactctaa a                                              21

<210> SEQ ID NO 76
<211> LENGTH: 21
<212> TYPE: DNA
<213> ORGANISM: Glycine max

<400> SEQUENCE: 76
taaatcttaa wtactaattt t                                              21

<210> SEQ ID NO 77
<211> LENGTH: 21
<212> TYPE: DNA
<213> ORGANISM: Glycine max

<400> SEQUENCE: 77
agcccaatga mtaatggagg a                                              21

<210> SEQ ID NO 78
<211> LENGTH: 21
<212> TYPE: DNA
<213> ORGANISM: Glycine max

<400> SEQUENCE: 78
ccgggaccac yaccaacgac g                                              21

<210> SEQ ID NO 79
<211> LENGTH: 21
<212> TYPE: DNA
<213> ORGANISM: Glycine max

<400> SEQUENCE: 79
ctgaaacaca matttcatac a                                              21

<210> SEQ ID NO 80
<211> LENGTH: 21
<212> TYPE: DNA
<213> ORGANISM: Glycine max
```

```
<400> SEQUENCE: 80
catacattaa raatctgaaa t                                              21

<210> SEQ ID NO 81
<211> LENGTH: 21
<212> TYPE: DNA
<213> ORGANISM: Glycine max

<400> SEQUENCE: 81
ccttccagaa yaatttgaaa a                                              21

<210> SEQ ID NO 82
<211> LENGTH: 21
<212> TYPE: DNA
<213> ORGANISM: Glycine max

<400> SEQUENCE: 82
tcttagataa ykggaaggaa a                                              21

<210> SEQ ID NO 83
<211> LENGTH: 21
<212> TYPE: DNA
<213> ORGANISM: Glycine max
<220> FEATURE:
<221> NAME/KEY: misc_feature
<222> LOCATION: (10)..(10)
<223> OTHER INFORMATION: miscellaneous SNP; not targeted SNP

<400> SEQUENCE: 83
cttagataay kggaaggaaa a                                              21

<210> SEQ ID NO 84
<211> LENGTH: 21
<212> TYPE: DNA
<213> ORGANISM: Glycine max

<400> SEQUENCE: 84
tgtatacttt yrattttaat a                                              21

<210> SEQ ID NO 85
<211> LENGTH: 21
<212> TYPE: DNA
<213> ORGANISM: Glycine max
<220> FEATURE:
<221> NAME/KEY: misc_feature
<222> LOCATION: (10)..(10)
<223> OTHER INFORMATION: miscellaneous SNP; not targeted SNP

<400> SEQUENCE: 85 gtatactttty rattttaata t                                             21

<210> SEQ ID NO 86
<211> LENGTH: 21
<212> TYPE: DNA
<213> ORGANISM: Glycine max

<400> SEQUENCE: 86
gatgatgata rcagcaagaa t                                              21

<210> SEQ ID NO 87
<211> LENGTH: 21
<212> TYPE: DNA
<213> ORGANISM: Glycine max
```

```
<400> SEQUENCE: 87
aacgaccacc yggaaatgac a                                      21

<210> SEQ ID NO 88
<211> LENGTH: 21
<212> TYPE: DNA
<213> ORGANISM: Glycine max

<400> SEQUENCE: 88
aagagacaag sagctcgcaa t                                      21

<210> SEQ ID NO 89
<211> LENGTH: 21
<212> TYPE: DNA
<213> ORGANISM: Glycine max

<400> SEQUENCE: 89
gctggttagt ratgccgcat c                                      21

<210> SEQ ID NO 90
<211> LENGTH: 21
<212> TYPE: DNA
<213> ORGANISM: Glycine max

<400> SEQUENCE: 90
actaattaag ytaatttgca c                                      21

<210> SEQ ID NO 91
<211> LENGTH: 21
<212> TYPE: DNA
<213> ORGANISM: Glycine max

<400> SEQUENCE: 91
gtgttgtgct wtatatacaa a                                      21

<210> SEQ ID NO 92
<211> LENGTH: 21
<212> TYPE: DNA
<213> ORGANISM: Glycine max

<400> SEQUENCE: 92
gccaaaggaa rtcactattg c                                      21

<210> SEQ ID NO 93
<211> LENGTH: 21
<212> TYPE: DNA
<213> ORGANISM: Glycine max

<400> SEQUENCE: 93 acttttcccct rgataaacaa a                                     21

<210> SEQ ID NO 94
<211> LENGTH: 21
<212> TYPE: DNA
<213> ORGANISM: Glycine max

<400> SEQUENCE: 94
ttaatttaga yggaaaatat t                                      21

<210> SEQ ID NO 95
<211> LENGTH: 21
<212> TYPE: DNA
<213> ORGANISM: Glycine max
```

```
<220> FEATURE:
<221> NAME/KEY: misc_feature
<222> LOCATION: (18)..(18)
<223> OTHER INFORMATION: miscellaneous SNP; not targeted SNP

<400> SEQUENCE: 95
ttttggaata sgagtcakta a                                              21

<210> SEQ ID NO 96
<211> LENGTH: 21
<212> TYPE: DNA
<213> ORGANISM: Glycine max
<220> FEATURE:
<221> NAME/KEY: misc_feature
<222> LOCATION: (4)..(4)
<223> OTHER INFORMATION: miscellaneous SNP; not targeted SNP

<400> SEQUENCE: 96
atasgagtca ktaatttcaa t                                              21

<210> SEQ ID NO 97
<211> LENGTH: 21
<212> TYPE: DNA
<213> ORGANISM: Glycine max

<400> SEQUENCE: 97
tgttacttct rgctattgaa a                                              21

<210> SEQ ID NO 98
<211> LENGTH: 21
<212> TYPE: DNA
<213> ORGANISM: Glycine max
<220> FEATURE:
<221> NAME/KEY: misc_feature
<222> LOCATION: (19)..(19)
<223> OTHER INFORMATION: miscellaneous SNP; not targeted SNP

<400> SEQUENCE: 98
gctattgaaa yatctcttkt t                                              21

<210> SEQ ID NO 99
<211> LENGTH: 21
<212> TYPE: DNA
<213> ORGANISM: Glycine max
<220> FEATURE:
<221> NAME/KEY: misc_feature
<222> LOCATION: (3)..(3)
<223> OTHER INFORMATION: miscellaneous SNP; not targeted SNP

<400> SEQUENCE: 99
aayatctctt kttttcaaac a                                              21

<210> SEQ ID NO 100
<211> LENGTH: 21
<212> TYPE: DNA
<213> ORGANISM: Glycine max

<400> SEQUENCE: 100
aaatcacaga maaatgtggc c                                              21

<210> SEQ ID NO 101
<211> LENGTH: 21
<212> TYPE: DNA
<213> ORGANISM: Glycine max
```

<400> SEQUENCE: 101
aaaacgatgc ygcacaacca c    21

<210> SEQ ID NO 102
<211> LENGTH: 21
<212> TYPE: DNA
<213> ORGANISM: Glycine max

<400> SEQUENCE: 102
tgtgccacaa ycaactgcgt a    21

<210> SEQ ID NO 103
<211> LENGTH: 21
<212> TYPE: DNA
<213> ORGANISM: Glycine max

<400> SEQUENCE: 103
attgtagtat rtgctttatg t    21

<210> SEQ ID NO 104
<211> LENGTH: 21
<212> TYPE: DNA
<213> ORGANISM: Glycine max

<400> SEQUENCE: 104
cttccaatct mactctcagc c    21

<210> SEQ ID NO 105
<211> LENGTH: 21
<212> TYPE: DNA
<213> ORGANISM: Glycine max

<400> SEQUENCE: 105
ctgatcatca ygcaattgca c    21

<210> SEQ ID NO 106
<211> LENGTH: 21
<212> TYPE: DNA
<213> ORGANISM: Glycine max

<400> SEQUENCE: 106
ctccaaaccc rtcaatgttc g    21

<210> SEQ ID NO 107
<211> LENGTH: 21
<212> TYPE: DNA
<213> ORGANISM: Glycine max

<400> SEQUENCE: 107
cttagttact ragggaaagg g    21

<210> SEQ ID NO 108
<211> LENGTH: 21
<212> TYPE: DNA
<213> ORGANISM: Glycine max

<400> SEQUENCE: 108
ccatcaagaa ytgcatagca t    21

<210> SEQ ID NO 109
<211> LENGTH: 21
<212> TYPE: DNA
<213> ORGANISM: Glycine max

```
<400> SEQUENCE: 109
ggaatccgag raccaaaagt a                                              21

<210> SEQ ID NO 110
<211> LENGTH: 21
<212> TYPE: DNA
<213> ORGANISM: Glycine max

<400> SEQUENCE: 110
acgaccatca magtgcttaa g                                              21

<210> SEQ ID NO 111
<211> LENGTH: 21
<212> TYPE: DNA
<213> ORGANISM: Glycine max

<400> SEQUENCE: 111
ttaaagctct ytgtatagga g                                              21

<210> SEQ ID NO 112
<211> LENGTH: 21
<212> TYPE: DNA
<213> ORGANISM: Glycine max

<400> SEQUENCE: 112
ttgtcatgca ytcattcgct c                                              21

<210> SEQ ID NO 113
<211> LENGTH: 21
<212> TYPE: DNA
<213> ORGANISM: Glycine max

<400> SEQUENCE: 113
tctttggttc rcggtagtat t                                              21

<210> SEQ ID NO 114
<211> LENGTH: 21
<212> TYPE: DNA
<213> ORGANISM: Glycine max

<400> SEQUENCE: 114
cttcagtcta yaagtggagc a                                              21

<210> SEQ ID NO 115
<211> LENGTH: 21
<212> TYPE: DNA
<213> ORGANISM: Glycine max
<220> FEATURE:
<221> NAME/KEY: misc_feature
<222> LOCATION: (14)..(14)
<223> OTHER INFORMATION: where n is a, t, c or g

<400> SEQUENCE: 115
tgaaaggaca racntgctta c                                              21

<210> SEQ ID NO 116
<211> LENGTH: 50
<212> TYPE: DNA
<213> ORGANISM: Artificial
<220> FEATURE:
<223> OTHER INFORMATION: synthetic oligonucleotide primer

<400> SEQUENCE: 116
gaaggtgacc aagttcatgc tgcatagtaa ttaattccat gtgcctatct               50
```

<210> SEQ ID NO 117
<211> LENGTH: 50
<212> TYPE: DNA
<213> ORGANISM: Artificial
<220> FEATURE:
<223> OTHER INFORMATION: synthetic oligonucleotide primer

<400> SEQUENCE: 117
gaaggtcgga gtcaacggat tgcatagtaa ttaattccat gtgcctatca          50

<210> SEQ ID NO 118
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 118
ctggaatgtt gaagatagaa tgaacgtgta                                30

<210> SEQ ID NO 119
<211> LENGTH: 46
<212> TYPE: DNA
<213> ORGANISM: Artificial
<220> FEATURE:
<223> OTHER INFORMATION: synthetic oligonucleotide primer

<400> SEQUENCE: 119
gaaggtgacc aagttcatgc tgatcatatc ctggtgaagg tgtctt              46

<210> SEQ ID NO 120
<211> LENGTH: 46
<212> TYPE: DNA
<213> ORGANISM: Artificial
<220> FEATURE:
<223> OTHER INFORMATION: synthetic oligonucleotide primer

<400> SEQUENCE: 120
gaaggtcgga gtcaacggat tgatcatatc ctggtgaagg tgtcta              46

<210> SEQ ID NO 121
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 121
gaaaattgct gcatcagcac tacatgtt                                  28

<210> SEQ ID NO 122
<211> LENGTH: 51
<212> TYPE: DNA
<213> ORGANISM: Artificial
<220> FEATURE:
<223> OTHER INFORMATION: synthetic oligonucleotide primer

<400> SEQUENCE: 122
gaaggtgacc aagttcatgc taaggatgga tgatatgcat cattattttc a        51

<210> SEQ ID NO 123
<211> LENGTH: 49
<212> TYPE: DNA
<213> ORGANISM: Artificial
<220> FEATURE:
<223> OTHER INFORMATION: synthetic oligonucleotide primer

<400> SEQUENCE: 123
gaaggtcgga gtcaacggat tggatggatg atatgcatca ttattttcg            49

<210> SEQ ID NO 124
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 124
ctcttctaag acatttccca atccgataa                                  29

<210> SEQ ID NO 125
<211> LENGTH: 43
<212> TYPE: DNA
<213> ORGANISM: Artificial
<220> FEATURE:
<223> OTHER INFORMATION: synthetic oligonucleotide primer

<400> SEQUENCE: 125
gaaggtgacc aagttcatgc tacttgtgca ccggaagcag cta                  43

<210> SEQ ID NO 126
<211> LENGTH: 42
<212> TYPE: DNA
<213> ORGANISM: Artificial
<220> FEATURE:
<223> OTHER INFORMATION: synthetic oligonucleotide primer

<400> SEQUENCE: 126
gaaggtcgga gtcaacggat tcttgtgcac cggaagcagc tg                   42

<210> SEQ ID NO 127
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 127
cccaagccag ctagtgtaat gagat                                      25

<210> SEQ ID NO 128
<211> LENGTH: 45
<212> TYPE: DNA
<213> ORGANISM: Artificial
<220> FEATURE:
<223> OTHER INFORMATION: synthetic oligonucleotide primer

<400> SEQUENCE: 128
gaaggtgacc aagttcatgc ttgtaccagt actcagccca atgaa                45

<210> SEQ ID NO 129
<211> LENGTH: 44
<212> TYPE: DNA
<213> ORGANISM: Artificial
<220> FEATURE:
<223> OTHER INFORMATION: synthetic oligonucleotide primer

<400> SEQUENCE: 129
gaaggtcgga gtcaacggat tgtaccagta ctcagcccaa tgac                 44

```
<210> SEQ ID NO 130
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 130
gatccaaagc gttggtcctc catta                                           25

<210> SEQ ID NO 131
<211> LENGTH: 47
<212> TYPE: DNA
<213> ORGANISM: Artificial
<220> FEATURE:
<223> OTHER INFORMATION: synthetic oligonucleotide primer

<400> SEQUENCE: 131
gaaggtgacc aagttcatgc tcattgtcat caatcgcaga atgtgta                   47

<210> SEQ ID NO 132
<211> LENGTH: 47
<212> TYPE: DNA
<213> ORGANISM: Artificial
<220> FEATURE:
<223> OTHER INFORMATION: synthetic oligonucleotide primer

<400> SEQUENCE: 132
gaaggtcgga gtcaacggat tcattgtcat caatcgcaga atgtgtc                   47

<210> SEQ ID NO 133
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 133
atggttatgt tgcaaagcgc aaagcaat                                        28

<210> SEQ ID NO 134
<211> LENGTH: 48
<212> TYPE: DNA
<213> ORGANISM: Artificial
<220> FEATURE:
<223> OTHER INFORMATION: synthetic oligonucleotide primer

<400> SEQUENCE: 134
gaaggtgacc aagttcatgc tacacaaagt tgcagacttc aacaatga                  48

<210> SEQ ID NO 135
<211> LENGTH: 47
<212> TYPE: DNA
<213> ORGANISM: Artificial
<220> FEATURE:
<223> OTHER INFORMATION: synthetic oligonucleotide primer

<400> SEQUENCE: 135
gaaggtcgga gtcaacggat tcacaaagtt gcagacttca acaatgg                   47

<210> SEQ ID NO 136
<211> LENGTH: 26
<212> TYPE: DNA
<213> ORGANISM: Artificial
<220> FEATURE:
<223> OTHER INFORMATION: synthetic oligonucleotide primer
```

```
<400> SEQUENCE: 136
gcacgatgca ttacttccac actcaa                                          26

<210> SEQ ID NO 137
<211> LENGTH: 52
<212> TYPE: DNA
<213> ORGANISM: Artificial
<220> FEATURE:
<223> OTHER INFORMATION: synthetic oligonucleotide primer

<400> SEQUENCE: 137
gaaggtgacc aagttcatgc tctatttatg ctttccaaaa taagaaaacg aa             52

<210> SEQ ID NO 138
<211> LENGTH: 52
<212> TYPE: DNA
<213> ORGANISM: Artificial
<220> FEATURE:
<223> OTHER INFORMATION: synthetic oligonucleotide primer

<400> SEQUENCE: 138
gaaggtcgga gtcaacggat tctatttatg ctttccaaaa taagaaaacg ag             52

<210> SEQ ID NO 139
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 139
gcttataata arcaactcag cctaatgcaa                                      30

<210> SEQ ID NO 140
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 140
gaaggtgacc aagttcatgc taaaccacca gaatcgggag c                         41

<210> SEQ ID NO 141
<211> LENGTH: 44
<212> TYPE: DNA
<213> ORGANISM: Artificial
<220> FEATURE:
<223> OTHER INFORMATION: synthetic oligonucleotide primer

<400> SEQUENCE: 141
gaaggtcgga gtcaacggat tgctaaacca ccagaatcgg gagt                      44

<210> SEQ ID NO 142
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 142
aatcactgaa tattggaggc attcccata                                       29
```

```
<210> SEQ ID NO 143
<211> LENGTH: 47
<212> TYPE: DNA
<213> ORGANISM: Artificial
<220> FEATURE:
<223> OTHER INFORMATION: synthetic oligonucleotide primer

<400> SEQUENCE: 143
gaaggtgacc aagttcatgc tcttcataat cccaacactt ttccta          47

<210> SEQ ID NO 144
<211> LENGTH: 47
<212> TYPE: DNA
<213> ORGANISM: Artificial
<220> FEATURE:
<223> OTHER INFORMATION: synthetic oligonucleotide primer

<400> SEQUENCE: 144
gaaggtcgga gtcaacggat tcttcataat cccaacactt ttccctg          47

<210> SEQ ID NO 145
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 145
ggcataaaag cattggtttt ctttgcattt                              30

<210> SEQ ID NO 146
<211> LENGTH: 23
<212> TYPE: DNA
<213> ORGANISM: Artificial Sequence
<220> FEATURE:
<223> OTHER INFORMATION: D-Sb-Rps1k-F forward primer

<400> SEQUENCE: 146
tgaagctgct aaaccaccag aat                                     23

<210> SEQ ID NO 147
<211> LENGTH: 30
<212> TYPE: DNA
<213> ORGANISM: Artificial Sequence
<220> FEATURE:
<223> OTHER INFORMATION: D-Sb-Rps1k-R reverse primer

<400> SEQUENCE: 147
aattgctaag gtcaatcact gaatattgga                              30

<210> SEQ ID NO 148
<211> LENGTH: 16
<212> TYPE: DNA
<213> ORGANISM: Artificial Sequence
<220> FEATURE:
<223> OTHER INFORMATION: D-Sb-Rps1k-FM resistant probe

<400> SEQUENCE: 148
attcccatag ctcccg                                             16

<210> SEQ ID NO 149
<211> LENGTH: 17
<212> TYPE: DNA
<213> ORGANISM: Artificial Sequence
<220> FEATURE:
<223> OTHER INFORMATION: D-Sb-Rps1k-VC susceptible probe
```

<400> SEQUENCE: 149
cattcccata actcccg                                                    17

<210> SEQ ID NO 150
<211> LENGTH: 121
<212> TYPE: DNA
<213> ORGANISM: Artificial Sequence
<220> FEATURE:
<223> OTHER INFORMATION: NCSB_000559 SNP marker

<400> SEQUENCE: 150
cataagccat atccgaacag accttggtct tggaaaattg ctgcatcagc actacatgtt      60
tagacacctt caccaggata tgatcgtgca tggttattag tggttgctac ttgcttgcac     120
t                                                                    121

<210> SEQ ID NO 151
<211> LENGTH: 121
<212> TYPE: DNA
<213> ORGANISM: Artificial Sequence
<220> FEATURE:
<223> OTHER INFORMATION: Gmax7x198_656813 SNP marker

<400> SEQUENCE: 151
cactctgcgc aatggaattc taagggacca ctggaatgtt gaagatagaa tgaacgtgta      60
tgataggcac atggaattaa ttactatgcc aaattcaaga aacttatcag gggctgaaaa     120
t                                                                    121

<210> SEQ ID NO 152
<211> LENGTH: 121
<212> TYPE: DNA
<213> ORGANISM: Artificial Sequence
<220> FEATURE:
<223> OTHER INFORMATION: SNP18196 SNP marker

<400> SEQUENCE: 152
tccatcctct aggtctacat tgctactatc aaaggatgga tgatatgcat cattattttc      60
gtttatcgga ttgggaaatg tcttagaaga ggatgcatga ctaaatttt tcggccacca     120 c                                                                    121

<210> SEQ ID NO 153
<211> LENGTH: 121
<212> TYPE: DNA
<213> ORGANISM: Artificial Sequence
<220> FEATURE:
<223> OTHER INFORMATION: NCSB_000575 SNP marker

<400> SEQUENCE: 153
accgtacata tagcatgagt gcatgacata agccccaagc cagctagtgt aatgagatac      60
cagctgcttc cggtgcacaa gtctttccta aaaatacttt aattccacac ccttgtgcat     120
c                                                                    121

<210> SEQ ID NO 154
<211> LENGTH: 121
<212> TYPE: DNA
<213> ORGANISM: Artificial Sequence
<220> FEATURE:
<223> OTHER INFORMATION: Gmax7x259_44054  SNP marker

```
<400> SEQUENCE: 154
gttctaggca atggtgcact gctgtgctta gaggagttgt accagtactc agcccaatga    60
ctaatggagg accaacgctt tggatcatcg ccgacgatgc aacagagatc aatttattca   120
g                                                                  121

<210> SEQ ID NO 155
<211> LENGTH: 121
<212> TYPE: DNA
<213> ORGANISM: Artificial Sequence
<220> FEATURE:
<223> OTHER INFORMATION: SNP18188   SNP marker

<400> SEQUENCE: 155
ctttattata ttgcaggcta agtcaaatgg tgatggttat gttgcaaagc gcaaagcaat    60
gacacattct gcgattgatg acaatgagca tcattcatgc aatttccaga aaatctaag   120 c                                                                  121

<210> SEQ ID NO 156
<211> LENGTH: 121
<212> TYPE: DNA
<213> ORGANISM: Artificial Sequence
<220> FEATURE:
<223> OTHER INFORMATION: Gmax7x259_98606 SNP marker

<400> SEQUENCE: 156
aattttgttg atgataaagg tagccaattt gagcacacaa agttgcagac ttcaacaatg    60
gcattgagtg tggaagtaat gcatcgtgca atgattaca ctttagccat ctggcctatg   120
a                                                                  121

<210> SEQ ID NO 157
<211> LENGTH: 145
<212> TYPE: DNA
<213> ORGANISM: Artificial Sequence
<220> FEATURE:
<223> OTHER INFORMATION: BARC_064351_18628 SNP marker

<400> SEQUENCE: 157
ctgttcgagc tgctgagagg tcaggcattt taatgaagct ttgaatgttt aaactcttct    60
atctctattt atgctttcca aaataagaaa acgagttgca ttaggctgag ttgyttatta   120
taagcttgat cattgttcac aataa                                        145

<210> SEQ ID NO 158
<211> LENGTH: 198
<212> TYPE: DNA
<213> ORGANISM: Artificial Sequence
<220> FEATURE:
<223> OTHER INFORMATION: BARC_064351_18631 SNP marker

<400> SEQUENCE: 158
attcttcttc aatgtcagtt ttatatatta tactcttcac ttttgaagct gctaaaccac    60
cagaatcggg agctatggga atgcctccaa tattcagtga ttgaccttag caattatatt   120
aagtggcttt attcttctgt ggccttaaat ttccataacc aacaataaat ttgattaact   180
tatctggttt ctggagac                                                198

<210> SEQ ID NO 159
<211> LENGTH: 121
<212> TYPE: DNA
<213> ORGANISM: Artificial Sequence
```

```
<220> FEATURE:
<223> OTHER INFORMATION: NCSB_000582 SNP marker

<400> SEQUENCE: 159
gaatgatgaa ccccgtatgc aacatttaaa ctactcttca taatcccaac acttttccct      60
ggataaacaa atgcaaagaa aaccaatgct tttatgccaa aataatatat gtatttattt     120
g                                                                     121
```

SOYBEAN MARKERS LINKED TO PHYTOPHTHORA RESISTANCE

This application claims the benefit of U.S. Provisional Application No. 61/777,575 which was filed in the U.S. Patent and Trademark Office on Mar. 12, 2013, the entire disclosure of which is hereby incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "Markers Linked to Phytophthora", created on Dec. 11, 2012, and having a size of 29,172 bytes and is filed concurrently with the specification. The sequence listing contained in this ASCII formatted document is part of the specification and is herein incorporated by reference in its entirety.

FIELD OF THE DISCLOSURE

The present disclosure relates to plant disease resistance. In some embodiments, the disclosure relates to *phytophthora* resistance in soybean. In particular embodiments, the disclosure relates to compositions and methods for identifying a *phytophthora* resistance trait in an organism. Examples include molecular markers that are tightly linked to *phytophthora* resistance traits and amplification detection assays that can detect the molecular markers that are tightly linked to *phytophthora* resistance traits. Further embodiments relate to compositions and methods for introducing a *phytophthora* resistance trait into a host organism, for example, by using molecular markers tightly linked to *phytophthora* resistance.

BACKGROUND

The soybean, *Glycine max*, is one of the major economic crops grown worldwide as a primary source of vegetable oil and protein. Growing demand for low cholesterol and high fiber diets has increased soybean's importance as a food. Over 10,000 soybean varieties have now been introduced into the United States, of which a limited number form the genetic base of lines developed from hybridization and selection programs. Johnson and Bernard, *The Soybean*, Norman Ed., Academic Press, N.Y., pp. 1-73, 1963.

*Phytophthora* is a highly destructive disease in soybean, and is only second to soybean cyst nematode in causing damage to soybean crops. This disease causes an annual yield loss of $300 million dollars (US) in North America (Wrather, J. A., and S. R. Koenning, (2006) Estimates of disease effects on soybean yields in the United States 2003 to 2005. *J Nematol* 38: 173-180), and occurs in most of the soybean-growing areas in many different countries. *Phytophthora sojae*, is a soilborne, oomycete pathogen and can cause *Phytophthora* root and stem rot (PRR), pre- and post-emergence of damping-off, yellowing and wilting of lower leaves, and death of soybean plants. More than fifty-five races of *P. sojae* have been identified (Slaminko et al., (2010) Multi-year evaluation of commercial soybean lines for resistance to *Phytophthora sojae*. *Plant Disease* 94). Developing soybean line resistance is one of the primary methods to control this disease. The Rps1-c (50%), Rps1-k (40%), and Rps1-a (10%) traits are the most commonly used genes that are introgressed into germplasm to provide protection to *P. sojae* (Slaminko et al., 2010).

Markers that are linked to the *phytophthora* resistance trait, Rps1-k, include RFLPs, SSRs and SNPs. The markers identified in this disclosure can be used for *phytophthora* resistance genotyping to support a breeding program. Using the presently disclosed markers to perform *phytophthora* resistance genotyping in support of a breeding program provides: cost and time savings; early selection of desired progeny; and more accurate and rapid commercialization of *phytophthora* resistant soybean varieties.

BRIEF SUMMARY OF THE DISCLOSURE

Molecular markers that are linked to a *phytophthora* resistance phenotype may be used to facilitate marker-assisted selection for the *phytophthora* resistance trait in soybean. Marker-assisted selection provides significant advantages with respect to time, cost, and labor, when compared to *phytophthora* resistance phenotyping. Surprisingly, it is disclosed herein that among 115 SNP markers identified to be within or near the *phytophthora* disease resistance QTL regions in the soybean genome that were polymorphic in parent genotypes, only 10 were linked to the *phytophthora* resistance trait. These 10 SNP markers offer superior utility in marker-assisted selection of *phytophthora* resistant soybean varieties.

Described herein as embodiments are nucleic acid molecular markers that are linked to (e.g., linked; tightly linked; or extremely tightly linked) a *phytophthora* resistance phenotype. In particular embodiments, the molecular markers may be SNP markers. Also described herein are methods of using nucleic acid molecular markers that are linked to a *phytophthora* resistance phenotype, for example and without limitation, to identify plants with a *phytophthora* resistance phenotype; to introduce a *phytophthora* resistance phenotype into new plant genotypes (e.g., through marker-assisted breeding or genetic transformation); and to cultivate plants that are likely to have a *phytophthora* resistance phenotype.

In one embodiment, are means for introducing a *phytophthora* resistance phenotype to soybean and means for identifying plants having a *phytophthora* resistance phenotype. In some embodiments, a means for introducing a *phytophthora* resistance phenotype into soybean may be a marker that is linked (e.g., linked; tightly linked; or extremely tightly linked) to a *phytophthora* resistance phenotype. In some embodiments, a means for identifying plants having a *phytophthora* resistance phenotype may be a probe that specifically hybridizes to a marker that is linked (e.g., linked; tightly linked; or extremely tightly linked) to a *phytophthora* resistance phenotype.

In one embodiment, methods of identifying a soybean plant that displays resistance to *phytophthora* infestation, comprising detecting in germplasm of the soybean plant at least one allele of a marker locus are provided. The marker locus is located within a chromosomal interval comprising and flanked by NCSB_000559 and NCSB_000582; and at least one allele is associated with *phytophthora* resistance. The marker locus can be selected from any of the following marker loci NCSB_000559, Gmax7x198_656813, SNP18196, NCSB_000575, Gmax7x259_44054, SNP18188, Gmax7x259_98606, BARC_064351_18628, BARC_064351_18631, and NCSB_000582, as well as any other marker that is linked to these markers. The marker locus can be found on chromosome 3, within the interval comprising and flanked by NCSB_000559 and NCSB_000582, and comprises at least one allele that is associated with *phytophthora* resistance. Soybean plants identified by this method are also of interest.

In another embodiment, methods for identifying soybean plants with resistance to *phytophthora* infestation by detecting a haplotype in the germplasm of the soybean plant are provided. The haplotype comprises alleles at one or more marker loci, wherein the one or more marker loci are found on chromosome 3 within the interval comprising and, flanked by, PZE-NCSB_000559 and NCSB_000582. The haplotype comprises alleles at one or more marker loci, wherein the one or more marker loci are found on chromosome 3 and are selected from the group consisting NCSB_000559, Gmax7x198_656813, SNP18196, NCSB_000575, Gmax7x259_44054, SNP18188, Gmax7x259_98606, BARC_064351_18628, BARC_064351_18631, and NCSB_000582. The haplotype is associated with *phytophthora* resistance.

In a further embodiment, methods of selecting plants with resistance to *phytophthora* infestation are provided. In one aspect, a first soybean plant is obtained that has at least one allele of a marker locus wherein the allele is associated with *phytophthora* resistance. The marker locus can be found on chromosome 3, within the interval comprising and flanked by NCSB_000559 and NCSB_000582. The first soybean plant can be crossed to a second soybean plant, and the progeny resulting from the cross can be evaluated for the allele of the first soybean plant. Progeny plants that possess the allele from the first soybean plant can be selected as having resistance to *phytophthora*. Soybean plants selected by this method are also of interest.

Also described herein are plants and plant materials that are derived from plants having a *phytophthora* resistance phenotype as identified using molecular markers described herein. Thus, soybean plants that are produced by marker-assisted selection using one or more molecular marker(s) that are linked to a *phytophthora* resistance phenotype are described.

BRIEF DESCRIPTION OF THE FIGURES

FIG. 3 further illustrates a chromosomal interval. This interval, located on chromosome 3, comprises and is flanked by PZE-NCSB_000559 and NCSB_000582. A subinterval of chromosomal interval NCSB_000559 and NCSB_000582 is NCSB_000575 and Gmax7x259_44054.

DETAILED DESCRIPTION

I. Overview of Several Embodiments

Figure 1:
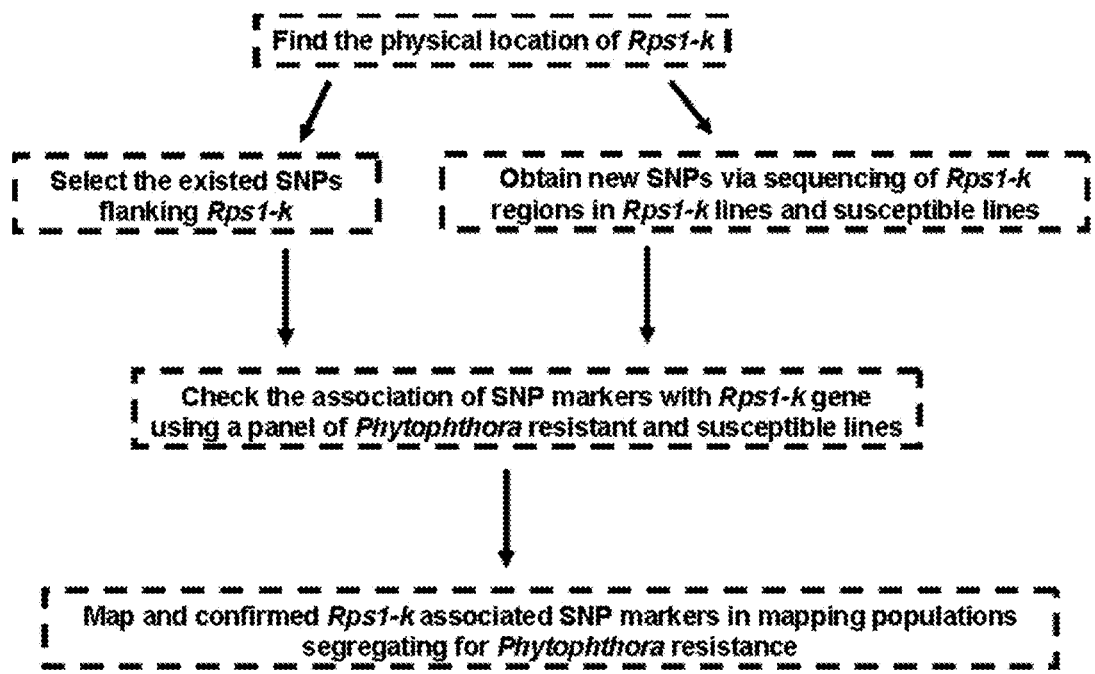
FIG. 1 illustrates the strategy of Rps1-k specific SNP marker development.

Particular embodiments include ten exemplary SNP markers (NCSB_000559, Gmax7x198_656813, SNP18196, NCSB_000575, Gmax7x259_44054, SNP18188, Gmax7x259_98606, BARC_064351_18628, BARC_064351_8631, and NCSB_000582) that show co-segregation with the *phytophthora* resistance trait, Rps1-k, in the tested soybean lines.

Markers that co-segregate with *phytophthora* resistance are linked to this trait, and therefore may be useful in marker-assisted selection and breeding. Also disclosed herein is a strategy used to identify the exemplary SNP markers linked to *phytophthora* resistance. In addition, an amplification detection assay that can detect the exemplary SNP markers is disclosed herein. The physical map positions of these exemplary SNP markers in the *Glycine max* genome are provided. Using the exemplary SNP markers described herein, a specific fret-based amplification assay using the KBiosciences Competitive Allele-Specific PCR SNP genotyping system (KASPAR™) and the TAQMAN™ hydrolysis probe assay was developed to rapidly and accurately identify plants carrying the *phytophthora* resistance trait. While embodiments of the disclosure are described with reference to the exemplary SNP markers linked to *phytophthora* resistance, those of skill in the art will appreciate that additional, equivalent markers may be identified using the techniques described herein. SNP markers linked to *phytophthora* resistance may be used, for example, in *phytophthora* genotyping to select *phytophthora* resistant plants from soybean breeding populations.

*Phytophthora* infestation may be caused by one or more different strains of *Phytophthora* spp. The resistance for this disease may be provided by different resistant genes located on different linkage groups. See, e.g., Table 1.

The strategy described herein is used to identify markers in other unknown linkage groups that are linked to *phytophthora* resistance. Thus, methods for identifying such markers and an amplification method for detecting the markers in plant tissue are provided. The general strategy is also used to map other traits of interest. The strategy is more efficient than traditional mapping strategies and may be particularly useful in molecular breeding programs.

TABLE 1

Sources of *phytophthora* resistance reported in the literature.

| Locus | Linkage Group | Chromosomal Location | Reference |
|---|---|---|---|
| Rps1 | N | Gm03 | Bernard, R. L. (1957) *Agron. J.* 49:391 |
| Rps2 | J | Gm16 | Kilen, T. C. (1974) *Crop Sci.* 14:260-262. |
| Rps3 | F | Gm13 | Mueller, E. H. (1978) *Phytopathology* 68:1318-1322. |
| Rps4 | G | Gm18 | Athow, K. L. (1980) *Phytopathology* 70: 977-980. |
| Rps5 | G | Gm18 | Buzzell, R. I. (1981) *Soybean Genet. Newsl.* 8:30-33. |
| Rps6 | G | Gm18 | Athow, K. L. (1982) *Phytopathology* 72: 1564-1567. |
| Rps7 | N | Gm18 | Anderson, T. R. (1992) *Plant Dis.* 76: 958-959. |
| Rps8 | A2 or F | Gm08 | Burnham, K. D. (2003) *Crop Sci.* 43: 101-105. |

II. Terms

Mapping population: As used herein, the term "mapping population" may refer to a plant population used for gene mapping. Mapping populations are typically obtained from controlled crosses of parent genotypes. Decisions on the selection of parents and mating design for the development of a mapping population, and the type of markers used, depend upon the gene to be mapped, the availability of markers, and the molecular map. The parents of plants within a mapping population must have sufficient variation for the trait(s) of interest at both the nucleic acid sequence and phenotype level. Variation of the parents' nucleic acid sequence is used to trace recombination events in the plants of the mapping population. The availability of informative polymorphic markers is dependent upon the amount of nucleic acid sequence variation.

Backcrossing: Backcrossing methods may be used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

The term "allele" refers to one of two or more different nucleotide sequences that occur at a specific locus.

An "amplicon" is amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid for a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Phytozome website, which is publicly available on the internet.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to sequence, polymorphisms at a particular locus, such as a single marker locus, or sequence polymorphisms at multiple loci along a chromosomal segment in a given genome. The former can also be referred to as "marker haplotypes" or "marker alleles", while the latter can be referred to as "long-range haplotypes".

An allele is "associated with" a trait when it is linked to it and when the presence of the allele is an indicator that the desired trait or trait form will occur in a plant comprising the allele.

KBiosciences Competitive Allele-Specific PCR SNP genotyping system (KASPAR™): KASPAR™ is a commercially available homogeneous fluorescent system for determining SNP genotypes (KBiosciences Ltd., Hoddesdon, UK). A KASPAR™ assay comprises an SNP-specific "assay mix," which contains three unlabelled primers, and a "reaction mix," which contains all the other required components; for example, a universal fluorescent reporting system. In addition to these mixes, the user provides, inter alia, a FRET-capable plate reader, microtitre plate(s), and DNA samples that contain about 5 ng/L DNA.

Chromosomal interval: A chromosomal interval designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The term "chromosomal interval" designates any and all intervals defined by any of the markers set forth in this invention. A chromosomal interval that correlates with *phytophthora* resistance is provided. This interval, located on chromosome 3, comprises and is flanked by PZE-NCSB_000559 and NCSB_000582. A subinterval of chromosomal interval NCSB_000559 and NCSB_000582 is NCSB_000575 and Gmax7×259_44054.

A typical KASPAR™ assay comprises the steps of: allele-specific primer design; preparation of reaction mix including the allele-specific primers; admixing the reaction mix to DNA samples in a microtitre plate; thermocycling; reading the plate in a fluorescent plate reader, and plotting and scoring the fluorescent data. Data from each sample are plotted together on a 2-D graph, where the x- and y-axes correspond to fluorophore excitation. Samples having the same SNP genotype cluster together on the plot (i.e., A/A; A/a; and a/a). More technical information about the KASPAR™ system, including a guide of solutions to common problems, is obtainable from KBiosciences Ltd. (e.g., the *KASPar SNP Genotyping System Reagent Manual*).

The TAQMAN™ hydrolysis probe assay is another commercially available homogeneous fluorescent system for determining SNP genotypes (Roche Technologies, Indianapolis, Ind.). A TAQMAN™ reaction relies on the 5'-3' exonuclease activity of the Taq polymerase to cleave a FRET oligonucelotide probe during hybridization of the probe to a complementary target sequence. The dual-labeled oligonucleotide probe is designed to overlap the SNP molecular marker. The dual-labeled probe contains both a fluorophore and a quencher. The release of the fluorophore and the resulting separation of the fluorophore from the quencher allows the fluorophore to release a fluorescent signal. The fluorescent signal indicates the presence of the flanking/transgene insert sequence due to successful amplification and hybridization.

As in other real-time PCR methods, the resulting fluorescence signal permits quantitative measurements of the accumulation of the product during the exponential stages of the PCR. The TAQMAN™ assay comprises an assay mix, which contains two unlabelled primers and a dual-labeled probe, and all the other required components. In addition to these mixes, the user provides, inter alia, a FRET-capable plate reader, microtitre plate(s), and DNA samples.

Linked, tightly linked, and extremely tightly linked: As used herein, linkage between genes or markers may refer to the phenomenon in which genes or markers on a chromosome show a measurable probability of being passed on together to individuals in the next generation. The closer two genes or markers are to each other, the closer to (1) this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in a plant, markers that are linked to the gene may be said to be linked to the phenotype. Thus, the term "linked" may refer to a relationship between a marker and a gene, or between a marker and a phenotype.

Because the proximity of two genes or markers on a chromosome is directly related to the probability that the genes or markers will be passed together to individuals in the next generation, the term "linked" may also refer herein to one or more genes or markers that are located within about 2.0 Mb of one another on the same chromosome. Thus, two "linked" genes or markers may be separated by about 2.1 Mb; 2.00 Mb; about 1.95 Mb; about 1.90 Mb; about 1.85 Mb; about 1.80 Mb; about 1.75 Mb; about 1.70 Mb; about 1.65 Mb; about 1.60 Mb; about 1.55 Mb; about 1.50 Mb; about 1.45 Mb; about 1.40 Mb; about 1.35 Mb; about 1.30 Mb; about 1.25 Mb; about 1.20 Mb; about 1.15 Mb; about 1.10 Mb; about 1.05 Mb; about 1.00 Mb; about 0.95 Mb; about 0.90 Mb; about 0.85 Mb; about 0.80 Mb; about 0.75 Mb; about 0.70 Mb; about 0.65 Mb; about 0.60 Mb; about 0.55 Mb; about 0.50 Mb; about 0.45 Mb; about 0.40 Mb; about 0.35 Mb; about 0.30 Mb; about 0.25 Mb; about 0.20 Mb; about 0.15 Mb; about 0.10 Mb; about 0.05 Mb; about 0.025 Mb; and about 0.01 Mb. Particular examples of markers that are "linked" to the *phytophthora* phenotype in soybean include nucleotide sequences on chromosome 3 (linkage group N) of the soybean genome.

As used herein, the term "tightly linked" may refer to one or more genes or markers that are located within about 0.5 Mb of one another on the same chromosome. Thus, two "tightly linked" genes or markers may be separated by about 0.6 Mb; about 0.55 Mb; 0.5 Mb; about 0.45 Mb; about 0.4 Mb; about 0.35 Mb; about 0.3 Mb; about 0.25 Mb; about 0.2 Mb; about 0.15 Mb; about 0.1 Mb; and about 0.05 Mb.

As used herein, the term "extremely tightly linked" may refer to one or more genes or markers that are located within about 100 kb of one another on the same chromosome. Thus, two "extremely tightly linked" genes or markers may be separated by about 125 kb; about 120 kb; about 115 kb; about 110 kb; about 105 kb; 100 kb; about 95 kb; about 90 kb; about 85 kb; about 80 kb; about 75 kb; about 70 kb; about 65 kb; about 60 kb; about 55 kb; about 50 kb; about 45 kb; about 40 kb; about 35 kb; about 30 kb; about 25 kb; about 20 kb; about 15 kb; about 10 kb; about 5 kb; and about 1 kb.

In view of the foregoing, it will be appreciated that markers linked to a particular gene or phenotype include those markers that are tightly linked, and those markers that are extremely tightly linked, to the gene or phenotype. Linked, tightly linked, and extremely tightly genetic markers of the *phytophthora* phenotype may be useful in marker-assisted breeding programs to identify *phytophthora* resistant soybean varieties, and to breed this trait into other soybean varieties to confer *phytophthora* resistance.

Locus: As used herein, the term "locus" refers to a position on the genome that corresponds to a measurable characteristic (e.g., a trait). An SNP locus is defined by a probe that hybridizes to DNA contained within the locus.

Marker: As used herein, a marker refers to a gene or nucleotide sequence that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). A "marker allele" refers to the version of the marker that is present in a particular individual.

The term marker as used herein may refer to a cloned segment of soybean chromosomal DNA, and may also or alternatively refer to a DNA molecule that is complementary to a cloned segment of soybean chromosomal DNA.

In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the plant genome. This is referred to herein as a "contiguous probe." The additional, contiguous nucleotide sequence is referred to as "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. All above-described markers may be used in some embodiments of the present disclosure.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: radiolabeling by nick translation; random priming; tailing with terminal deoxytransferase; or the like, where the nucleotides employed are labeled, for example, with radioactive $^{32}P$. Other labels which may be used include, for example and without limitation: Fluorophores (e.g., FAM and VIC); enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the genome so that the noncontiguous probe is genetically linked to the same gene or trait (e.g., *phytophthora* resistance). For example, in some embodiments, a noncontiguous probe is located within 500 kb; 450 kb; 400 kb; 350 kb; 300 kb; 250 kb; 200 kb; 150 kb; 125 kb; 100 kb; 0.9 kb; 0.8 kb; 0.7 kb; 0.6 kb; 0.5 kb; 0.4 kb; 0.3 kb; 0.2 kb; or 0.1 kb of the original marker on the soybean genome.

A probe may be an exact copy of a marker to be detected. A probe may also be a nucleic acid molecule comprising, or consisting of, a nucleotide sequence which is substantially identical to a cloned segment of the subject organism's (for example, soybean) chromosomal DNA. As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

The following are representative, non-limiting hybridization conditions.

Very High Stringency (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

High Stringency (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency (detects sequences that share at least 50% sequence identity): Hybridization in 6×SSC buffer at room temperature to 55° C. for 16-20 hours; wash at least twice in 2×-3×SSC buffer at room temperature to 55° C. for 20-30 minutes each.

With respect to all probes discussed, supra, the probe may comprise additional nucleic acid sequences, for example, promoters; transcription signals; and/or vector sequences. Any of the probes discussed, supra, may be used to define additional markers that are tightly-linked to a gene involved in *phytophthora* resistance, and markers thus identified may be equivalent to exemplary markers named in the present disclosure, and thus are within the scope of the disclosure.

Marker-assisted breeding: As used herein, the term "marker-assisted breeding" may refer to an approach to breeding directly for one or more complex traits (e.g., *phytophthora* resistance). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, obviating the need to maintain plants to maturity; and co-dominance of the isozyme marker alleles allows discrimination between homozygotes and heterozygotes. See, e.g., Rick (1983) in Tanksley and Orton, supra.

Quantitative trait locus: As used herein, the term "Quantitative trait locus" (QTL) may refer to stretches of DNA that have been identified as likely DNA sequences (e.g., genes, non-coding sequences, and/or intergenic sequences) that underlie a quantitative trait, or phenotype, that varies in degree, and can be attributed to the interactions between two or more DNA sequences (e.g., genes, non-coding sequences, and/or intergenic sequences) or their expression products and their environment. Quantitative trait loci (QTLs) can be molecularly identified to help map regions of the genome that contain sequences involved in specifying a quantitative trait.

As used herein, the term "QTL interval" may refer to stretches of DNA that are linked to the genes that underlie the QTL trait. A QTL interval is typically, but not necessarily, larger than the QTL itself. A QTL interval may contain stretches of DNA that are 5' and/or 3' with respect to the QTL.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Single-nucleotide polymorphism: As used herein, the term "single-nucleotide polymorphism" (SNP) may refer to a DNA sequence variation occurring when a single nucleotide in the genome (or other shared sequence) differs between members of a species or paired chromosomes in an individual. Within a population, SNPs can be assigned a minor allele frequency that is the lowest allele frequency at a locus that is observed in a particular population. This is simply the lesser of the two allele frequencies for single-nucleotide polymorphisms. Different populations are expected to exhibit at least slightly different allele frequencies. Particular populations may exhibit significantly different allele frequencies. In some examples, markers linked to *phytophthora* resistance are SNP markers.

SNPs may fall within coding sequences of genes, non-coding regions of genes, or in the intergenic regions between genes. SNPs within a coding sequence will not necessarily change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid, and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) *Nature* 409:928-33.

Trait or phenotype: The terms "trait" and "phenotype" are used interchangeably herein. For the purposes of the present disclosure, a trait of particular interest is *phytophthora* resistance.

III. QTL-Based Identification of Markers Linked to a Trait of Interest

A. Overview

In some embodiments, a trait (e.g., *phytophthora* resistance) is mapped using a strategy that is different from traditional mapping approaches. For example, a trait may be mapped according to a strategy that, for the sake of convenience, may be described as comprising 4 steps. In a first step, QTL interval target regions that correspond to a trait (e.g., Rps1-k) to be mapped may be determined. In a second step, markers (e.g., SNP markers) may be selected which are located within or near determined QTL intervals of the target genome (e.g., soybean genome). In a third step, specific primers may be designed that facilitate the genotyping of individual subjects with respect to selected markers. In particular examples, specific primers are designed for use in a KASPAR™ or TAQMAN™ genotyping assay in *phytophthora* resistant and susceptible soybean lines. In a fourth step, populations that show segregation for the trait may be screened using the specific primers to identify those markers that are linked to the trait. See, e.g., FIG. 1.

B. Markers Linked to a Trait of Interest and the Identification Thereof

Determination of QTL interval target regions and identification of markers.

QTLs may be determined by any technique available to those of skill in the art. For example, the physical positions of a QTL that corresponds to a particular trait of interest may be initially determined by reference to the location of genes that are known to contribute to the particular trait. In some embodiments, *phytophthora* resistance genes may be identified on different regions of chromosome 3. In some embodiments, the initially identified QTLs are grouped or divided into a less complicated or extensive list of QTLs that may have boundaries in the genome that are the same or different than the boundaries of the initially identified QTLs.

In some embodiments, a region of DNA may be selected that is likely to contain markers that are linked to the QTL trait. This region may be referred to as a QTL interval. For example, a QTL interval may be a region of DNA that includes the QTL and additional genomic DNA that is near the QTL in either, or both, the 5' and 3' directions. In some embodiments, a QTL interval may be about 4 Mb; about 3.5 Mb; about 3 Mb; about 2.5 Mb; about 2 Mb; about 1.5 Mb; 1 Mb; 0.5 Mb; or about 0.25 Mb.

In particular embodiments, the target genome may be searched to identify markers that are physically located in, near, or between the QTLs and QTL intervals. If a reference map containing the location of known markers is available for the target genome, the reference map may be used to identify markers. Nucleic acid sequences of the target genome may also be searched, for example, by software such as BLAST™. In some embodiments, SNP markers may be identified. In some embodiments, markers may be identified that are physically located in, near, or between QTLs and QTL intervals of the soybean genome that correspond to the *phytophthora* resistance trait. In particular examples, identified SNP markers that are physically located in, near, or between QTLs and QTL intervals of the soybean genome that correspond to the *phytophthora* resistance trait may be selected from the group consisting of the markers identified as being linked to *phytophthora* resistance and listed in Table 4A.

In other embodiments, particular markers may be selected from the identified markers that are physically located in, near, or between QTLs and QTL intervals that correspond to a trait of interest, which markers are polymorphic among the parental lines from which a mapping population will be generated. Polymorphism of a given marker among the parental lines is directly related to the ability to trace recombination events in a mapping population produced from the parental lines.

In particular examples, polymorphic markers among parental soybean lines are selected to screen *phytophthora* resistance mapping populations to determine which, if any, of the polymorphic markers are linked to the *phytophthora* resistance trait. Such markers may segregate so that one allele of the SNP marker appears exclusively in *phytophthora* resistant individuals, and the other allele of the SNP marker appears exclusively in *phytophthora* susceptible individuals. Mapping populations may be generated by crossing one variety that is *phytophthora* resistant with another variety that is *phytophthora* susceptible. In embodiments, a mapping population may comprise about 10, about 20, about 30, about 40, about 50, about 60, about 70, about 80, about 90, about 95, about 100, about 150, about 200, about 250, about 300, about 350, about 400, about 450, about 500, or more individuals. In some embodiments, *phytophthora* resistant soybean germplasm may be crossed with one or more *phytophthora* susceptible germplasm(s) to create mapping populations.

In some embodiments, the polymorphic markers may be single nucleotide polymorphisms (SNPs) linked to or within the gene or QTL corresponding to the *phytophthora* resistance trait of interest. These SNP markers may be detected by sequencing through the region containing the gene or QTL using any DNA sequencing methods known in the art, including but not limited to Sanger sequencing or high throughput sequencing ("Next Generation") methodologies that enable short or long sequence reads through the region of interest. In such embodiments, where genotyping by sequencing is used for the detection of SNP markers, primers corresponding to the flanking sequences of the region containing the SNPs in gene or QTL of interest may be used for the sequencing chemistries in order to sequence through the region of interest. In such embodiments, when different genotypes are used for sequencing through the region of interest for the detection of SNPs exemplified herein, other SNPs may be identified in addition to the SNPs exemplified herein. In such embodiments, the SNPs exemplified herein by themselves (individual SNPs) or in combination with other SNPs linked to exemplified sequences (haplotypes) may be utilized for differentiating genotypes towards marker assisted selection of plants for the *phytophthora* resistance trait of interest.

Primer design and linkage screening.

Oligonucleotide probes or primers may be designed to specifically detect markers that are physically located in, near, or between QTLs and QTL intervals that correspond to a trait of interest. In general, an oligonucleotide probe or primer may be designed that specifically hybridizes to only one allele of a marker. In some embodiments, two sets of oligonucleotide probes and primers are designed to detect an SNP marker, such that each specifically hybridizes to the SNP allele to which the other probe and primer does not specifically hybridize. As is understood by those of skill in the art, the length or composition of oligonucleotide probe and primers for a particular marker may be varied according to established principles without rendering the probe non-specific for one allele of the marker.

In some embodiments, the oligonucleotide probes may be primers. In specific embodiments, primers may be designed to detect markers in a KASPAR™ genotyping assay. In particular embodiments, primers may be designed to detect markers linked to the *phytophthora* resistance phenotype in soybean using a KASPAR™ genotyping assay. In these and further embodiments, the detection system may provide a high-throughput and convenient format for genotyping individuals in a mapping population, which may greatly facilitate the identification of individuals carrying a particular gene or trait, and may also greatly facilitate the implementation or execution of a marker-assisted selection program.

In specific embodiments, the oligonucleotide probes may be primers designed to detect markers in a TAQMAN® genotyping assay. This method utilizes primers specific to the marker closely linked to the *phytophthora* resistance gene and fluorescent labeled probes containing a single nucleotide polymorphism (SNP). The SNP probe associated with resistance is labeled with a fluorescent dye such as FAM while the probe associated with susceptibility is labeled with a different fluorescent dye such as VIC. The data is analyzed as the presence or absence of a fluorescent dye signal. The detection system may provide a high-throughput and convenient format such as multiplexing for genotyping individuals in a mapping population, which may greatly facilitate the identification of individuals carrying a particular gene or trait, and may also greatly facilitate the implementation or execution of a marker-assisted selection program.

Additional markers may be identified as equivalent to any of the exemplary markers named herein, for example, by determining the frequency of recombination between the exemplary marker and an additional marker. Such determinations may utilize a method of orthogonal contrasts based on the method of Mather (1931), *The Measurement of Linkage in Heredity*, Methuen & Co., London, followed by a test of maximum likelihood to determine a recombination frequency. Allard (1956) Hilgardia 24:235-78. If the value of the recombination frequency is less than or equal to 0.10 (i.e., 10%), then the additional marker is considered equivalent to the particular exemplary marker for the purposes of use in the presently disclosed methods.

Markers that are linked to any and all *phytophthora* resistance genes may be identified in embodiments of the disclosure. Further, markers that control any and all of resistance contributing loci for all *phytophthora* races may be identified in embodiments of the disclosure.

A means for providing *phytophthora* resistance in soybean may be an SNP marker allele, the detection of which SNP marker allele in soybean plants provides at least a strong indication that the plant comprising the nucleic acid sequence has the *phytophthora* resistance phenotype. In some examples, a means for providing *phytophthora* resistance in soybean is a marker selected from the group consisting of the markers described as being linked to *phytophthora* resistance listed in Table 4A. In particular examples, a means for providing *phytophthora* resistance in soybean is a marker selected from the group consisting of NCSB_000559, Gmax7x198_656813, SNP18196, NCSB_000575, Gmax7×259_44054, SNP18188, Gmax7×259_98606, BARC_064351_18628, BARC_064351_18631, and NCSB_000582.

A means for identifying soybean plants having the *phytophthora* resistance phenotype may be a molecule that presents a detectable signal when added to a sample obtained from a soybean plant having the *phytophthora* resistance genotype, but which means does not present a detectable signal when added to a sample obtained from a soybean plant that does not have the *phytophthora* resistance phenotype. Specific hybridization of nucleic acids is a detectable signal, and a nucleic acid probe that specifically hybridizes to an SNP marker allele that is linked to the *phytophthora* resistance phenotype may therefore be a means for identifying soybean plants having the *phytophthora* resistance phenotype. In some examples, a means for identifying soybean plants having the *phytophthora* resistance phenotype is a probe that specifically hybridizes to a marker that is linked to the *phytophthora* resistance phenotype.

B. Methods of Using Markers Linked to a Trait of Interest

Methods of using nucleic acid molecular markers that are linked to a trait of interest (e.g., *phytophthora* resistance in soybean) to identify plants having the trait of interest may result in a cost savings for plant breeders and producers, because such methods may eliminate the need to phenotype individual plants generated during development (for example, by crossing soybean plant varieties having *phytophthora* resistance with vulnerable plant varieties).

In particular embodiments, markers linked to *phytophthora* resistance in soybean may be used to transfer segment(s) of DNA that contain one or more determinants of *phytophthora* resistance. In particular embodiments, the markers may be selected from a group of markers comprising the markers listed in Table 4A and markers that are their equivalents. In some embodiments, a marker may be selected from the group consisting of NCSB_000559, Gmax7×198_656813, SNP18196, NCSB_000575, Gmax7×259_44054, SNP18188, Gmax7×259_98606, BARC_064351_18628, BARC_064351_18631, and NCSB_000582. In some embodiments, a method for using markers linked to *phytophthora* resistance in soybean to transfer segment(s) of DNA that contain one or more determinants of *phytophthora* resistance may comprise analyzing the genomic DNA of two parent plants with probes that are specifically hybridizable to markers linked to the *phytophthora* resistance phenotype; sexually crossing the two parental plant genotypes to obtain a progeny population, and analyzing those progeny for the presence of the markers linked to the *phytophthora* resistance phenotype; backcrossing the progeny that contain the markers linked to the *phytophthora* resistance phenotype to the recipient genotype to produce a first backcross population, and then continuing with a backcrossing program until a final progeny is obtained that comprises any desired trait(s) exhibited by the parent genotype and the *phytophthora* resistance phenotype. In particular embodiments, individual progeny obtained in each crossing and backcrossing step are selected by *phytophthora* marker analysis at each generation. In some embodiments, analysis of the genomic DNA of the two parent plants with probes that are specifically hybridizable to markers linked to *phytophthora* resistance phenotype reveals that one of the parent plants comprises fewer of the linked markers to which the probes specifically hybridize, or none of the linked markers to which the probes specifically hybridize. In some embodiments, individual progeny obtained in each cross and/or backcross are selected by the sequence variation of individual plants.

In some embodiments, markers linked to the *phytophthora* resistance phenotype may be used to introduce one or more determinants of *phytophthora* resistance into a plant (e.g., soybean) by genetic transformation. In particular embodiments, the markers may be selected from a group of markers comprising the markers listed in Table 4A and markers that are their equivalents. In some embodiments, a method for introducing one or more determinants of *phytophthora* resistance into a plant by genetic recombination may comprise analyzing the genomic DNA of a plant (e.g., soybean) with probes that are specifically hybridizable to markers linked to the *phytophthora* resistance phenotype to identify one or more determinants of *phytophthora* resistance in the plant; isolating a segment of the genomic DNA of the plant comprising the markers linked to the *phytophthora* resistance phenotype, for example, by extracting the genomic DNA and digesting the genomic DNA with one or more restriction endonuclease enzymes; optionally amplifying the isolated segment of DNA; introducing the isolated segment of DNA into a cell or tissue of a host plant; and analyzing the DNA of the host plant with probes that are specifically hybridizable to markers linked to the *phytophthora* resistance phenotype to identify the one or more determinants of *phytophthora* resistance in the host plant. In particular embodiments, the isolated segment of DNA may be introduced into the host plant such that it is stably integrated into the genome of the host plant.

In some embodiments, markers that are linked to the *phytophthora* resistance phenotype may be used to introduce one or more determinants of *phytophthora* resistance into other organisms, for example, plants. In particular embodiments, the markers can be selected from a group of markers listed in Table 4A and markers that are their equivalents. In some embodiments, a method for introducing one or more determinants of *phytophthora* resistance into an organism other than soybean may comprise analyzing the genomic DNA of a plant (e.g., a soybean plant) with probes that are specifically hybridizable to markers linked to the *phytophthora* resistance phenotype to identify one or more determinants of *phytophthora* resistance in the plant; isolating a segment of the genomic DNA of the plant comprising the one or more determinants of *phytophthora* resistance, for example, by extracting the genomic DNA and digesting the genomic DNA with one or more restriction endonuclease enzymes; optionally amplifying the isolated segment of DNA; introducing the isolated segment of DNA into an organism other than soybean; and analyzing the DNA of the organism other than soybean with probes that are specifically hybridizable to markers linked to the *phytophthora* resistance phenotype to identify the one or more determinants of *phytophthora* resistance in the organism. In other embodiments, the isolated segment of DNA may be introduced into the organism such that it is stably integrated into the genome of the organism.

In some embodiments, markers that are linked to the *phytophthora* resistance phenotype may be used to identify a plant with one or more determinants of *phytophthora* resistance. In some embodiments, the plant may be a soybean plant. In particular embodiments, nucleic acid molecules (e.g., genomic DNA or mRNA) may be extracted from a plant. The extracted nucleic acid molecules may then be contacted with one or more probes that are specifically hybridizable to markers linked to the *phytophthora* resistance phenotype. Specific hybridization of the one or more probes to the extracted nucleic acid molecules is indicative of the presence of one or more determinants of *phytophthora* resistance in the plant.

In some embodiments, markers that are linked to multiple determinants of *phytophthora* resistance may be used simultaneously. In other embodiments, markers that are linked to only one determinant of *phytophthora* resistance may be used. In specific examples, markers that are linked to *phytophthora* resistance with respect to one or more particular *Phytophthora* spp. may be used simultaneously For example, a plurality of markers that are linked to *phytophthora* resistance with respect to different *Phytophthora* spp. races may be used simultaneously.

The following examples are provided to illustrate certain particular features and/or embodiments. These examples should not be construed to limit the disclosure to the particular features or embodiments described.

EXAMPLES

Example 1: Marker Development Strategy

The following strategy was developed to identify novel SNP markers tightly linked to Rps1-k. Nucleotide sequences which encode the two Rps1-k disease proteins, NBS-LRR type disease resistance proteins Rps1-k-1 and Rps1-k-2, were identified in GenBank (Accession No: EU450800) based on the disclosure of Gao H. and Bhattacharyya M. K. (2008) The soybean-*Phytophthora* resistance locus Rps1-k encompasses coiled coil-nucleotide binding-leucine rich repeat-like genes and repetitive sequences. Gao and Bhattacharyya (2008) BMC Plant Biol 8:29. The bacterial artificial chromosome (BAC) sequence was divided into 37 fragments of about 5 kB and each fragment was BLASTed against the soybean genomic database located on the Phytozome website (phytozome.com) to identify its physical location in the soybean genome. Once the physical location of Rps1-k was identified, a set of single nucleotide polymorphism (SNP) markers were selected in the region from the soybean genomic database. KBioscience Competitive Allele-Specific PCR genotyping system (KASPAR™) assays were developed for the SNPs in the region and were screened against a panel of soybean plants that included Rps1-k, Rps1-a, and Rps1-c resistant and susceptible lines. By comparing the KASPAR™ genotyping data with the known phenotype of the plants from the panel, it was possible to identify the polymorphic SNP markers between Rps1-k, Rps1-a, Rps1-c resistant lines and susceptible lines. Additional validation of these selected polymorphic SNPs markers with mapping populations allowed identification of previously undescribed, novel markers that were tightly linked with Rps1-k, and are useful for soybean marker assisted selection (MAS) for *phytophthora* resistance. A schematic of this strategy is outlined in FIG. 1.

Example 2: Plant Material

Six mapping parents of 18 plant introduction (PI) lines were included in the marker screening panel. The panel included Rps1-k, Rps1-a, and Rps1-c resistant and susceptible lines that are listed in Table 2.

TABLE 2

Soybean lines used in the initial Rps1-k SNP marker screening. The "Trait" column indicates which lines were susceptible or resistant to *phytophthora*, and identifies the trait (Rps1-k, Rps1-c, and Rps1-a) associated with the *phytophthora* resistant lines.

| Lines | Entry | Trait |
|---|---|---|
| — | 75357-71 | susceptible |
| — | 75448 | Rps1-k |
| — | 20430-74 | Rps1-k |
| — | 20130-77 | Rps1-c |
| — | 20281 | Rps1-c |
| — | 75477 | susceptible |
| PI542044 | Kunitz | Rps1-k |
| PI547677 | L59-731 | Rps1-a |
| PI547405 | L61-4222 | Rps1-a |
| PI547679 | L61-5047 | Rps1 |
| PI547834 | L75-3735 | Rps1-c |
| — | Maverick | Rps1-k |
| PI547619 | L75-3901 | Rps1-c |
| PI547890 | L77-1794 | Rps1-k |
| PI547639 | L77-2015 | Rps1-k |
| PI547646 | L79-1380 | Rps1-c |
| PI547647 | L79-1404 | Rps1-c |
| PI547879 | L87-0482 | Rps1-k |
| PI591536 | L90-8003 | Rps1-k |
| PI591534 | L90-8047 | Rps1-k |
| PI591539 | L91-8558 | Rps1-k |
| PI591535 | L93-7290 | Rps1-k |
| PI548631 | Williams | susceptible |
| PI518670 | Williams79 | Rps1-c |

Three mapping populations were developed for use. The first population included 127 $F_{2:3}$ lines from a cross between 75357-71 (susceptible) and 75448 (Rps1-k resistant). The second population consisted of 204 $F_{2:3}$ lines from a cross between 20430-74 (Rps1-k resistant) and 20130-77 (Rps1-c resistant). The third population included 125 $F_{2:3}$ lines from a cross between 20281 (Rps1-c resistant) and 75477 (susceptible).

Example 3: DNA Extraction and Sample Preparation

Eight leaf discs per soybean plant were collected at the second-node stage. The DNA was extracted using the MAGATTRACT™ DNA extraction method (Qiagen, Valencia, Calif.) using the BIOCEL 1800™ DNA isolation system (Agilent Technologies, Santa Clara, Calif.). DNA was quantified using the NANODROP 8000™ Spectrophotometer (Thermo Scientific, Rockford, Ill.) per manufacturer's instructions. DNA from each of the 10 $F_3$ progenies was pooled together per $F_{2:3}$ line. The pooled DNA samples were diluted to 1-5 nanograms/microliter (ng/μl) for genotyping.

Example 4: *Phytophthora* Phenotyping

For each $F_{2:3}$ lines, 10 seeds were grown in a greenhouse. The cotyledons of the soybean plants were infected by *Phytophthora sojae*, race 4. The infected plants were observed and the number of plants which survived versus plants which were susceptible to the infestation were recorded. If all 10 plants survived, the $F_2$ phenotype was defined as 'r', indicating homologous Rps1-k resistance. If all 10 plants died after infestation, the $F_2$ phenotype was defined as 's', indicating homologous susceptible to Rps1-k. If the 10 plants produced a mixed population which was constituted of some living and some susceptible plants the $F_2$ phenotype was defined as 'h', which indicated that the plants were segregating for Rps1-k resistance.

Example 5: The KBioscience Competitive Allele-Specific PCR Genotyping System (KASPAR™)

The KASPAR™ genotyping system is comprised of two components (1) the SNP-specific assay (a combination of three unlabelled primers), and (2) the universal Reaction Mix, which contains all other required components including the universal fluorescent reporting system and a specially-developed Taq polymerase. The three primers, allele-specific 1 (A1), allele-specific 2 (A2), and common (C1), or reverse, (Table 4) were designed using the assay design algorithm of the workflow manager, Kraken (KBiosciences, Hoddesdon, Hertfordshire, UK).

An Assay Mix of the three primers was made, consisting of 12 micromolar (µM) each of A1 and A2 and 30 µM of C1. The universal Reaction Mix was diluted to 1× and an additional amount of $MgCl_2$ was added so that the final $MgCl_2$ concentration of Reaction Mix at 1× concentration was 1.8 millimolar (mM). DNA was dispensed into 384 well PCR plates at a concentration of 1-5 ng/µl per well and was dried down in the plates in a 65° C. oven for 1 hour and 15 minutes. The Assay Mix and universal Reaction Mix were combined in a 1:54 ratio and 4 µl was dispensed into the DNA plates using a liquid handler robot, so that the final amount of the Assay Mix in the plate was 0.07 µl and the final amount of the diluted Reaction Mix was 3.93 µl. GENEAMP PCR SYSTEM 9700™ machines (Applied Biosystems, Foster City, Calif.) were used for thermocycling with the following conditions: 94° C. for 15 minutes, 20 cycles of 94° C. for 10 seconds, 57° C. for 5 seconds, 72° C. for 10 seconds; 22 cycles of 94° C. for 10 seconds, 57° C. for 20 seconds, 72° C. for 40 seconds. After thermocycling was complete, allele-specific fluorescent intensities were read using a PHERASTAR® Spectrofluorometer (BMG LabTech, Cary, N.C.) at room temperature and data was uploaded to the Kraken system for analysis.

Example 6: Genotyping Data Analysis

Figure 2:
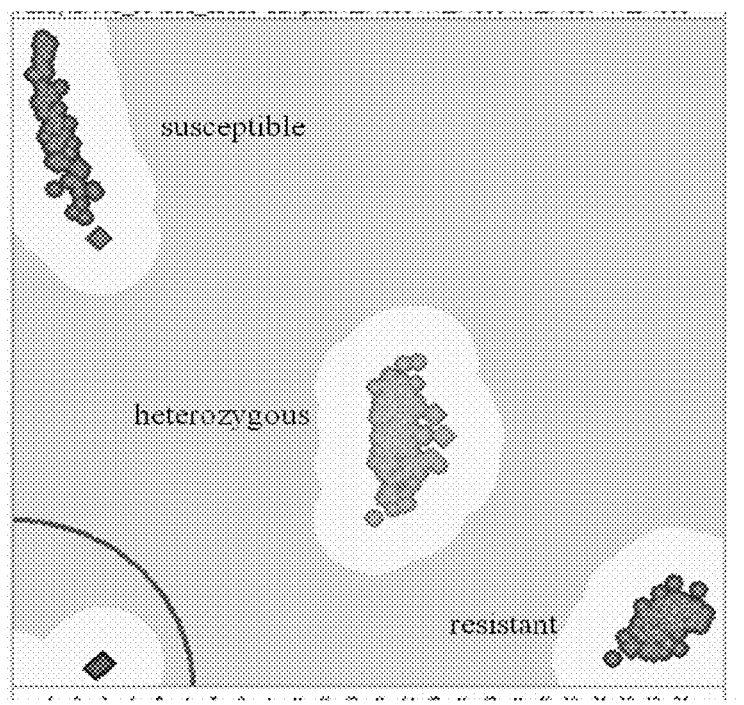
FIG. 2 includes an example of the results of a distribution graph of a KASPAR™ assay that was sorted based on Relative Fluorescence Units (RFU).

The KASPAR™ reaction incorporates the use of the fluorophores FAM and VIC into the A1 and A2 primers which were respectively designed to bind susceptible and resistant genotypes for each SNP marker. The passive reference dye ROX was also incorporated into the reaction to normalize variations in fluorophore signal caused by differences in well-to-well liquid volume. Using Kraken, the results of the KASPAR™ reactions for each sample was plotted on the x- and, y-axes of a graph. The x-axes were plotted with samples that resulted in reactions which produced FAM fluorescence and the y-axes were plotted with samples that resulted in reactions which produced VIC fluorescence. The different resistant and susceptible genotypes were determined according to the location of each sample clusters (FIG. 2).

A total of 115 independent KASPAR™ assays were developed to detect SNPs that were identified in the 1.7 to 4.9 megabase pair (Mbp) region on chromosome 3 (Table 3). The resulting 115 KASPAR™ assays were subsequently screened on the panel of soybean lines described in Table 2. The results of this screening via the KASPAR™ assays resulted in the identification of 24 novel markers. The novel SNP markers are listed in bold text within Table 3. Next, the 24 markers were used to screen the 3 mapping populations which were described in Example 2.

TABLE 3

List of the 115 SNP markers screened on the marker screening panel.

| Marker Name | Sequence | SNP | Position (bp) | Start (bp) | End (bp) |
|---|---|---|---|---|---|
| NCSB_000547 | SEQ ID NO: 1 | A/G | — | 1764856 | 1764901 |
| NCSB_000548 | SEQ ID NO: 2 | T/C | 1891835 | 1891775 | 1891895 |
| NCSB_000549 | SEQ ID NO: 3 | A/G | 1971666 | 1971634 | 1971754 |
| SNP5583_Magellan | SEQ ID NO: 4 | T/C | 1995295 | 1995235 | 1995355 |
| BARC_042969_08482 | SEQ ID NO: 5 | A/C | — | 1999380 | 2000006 |
| BARC_042969_08479 | SEQ ID NO: 6 | T/C | — | 1999446 | 2000006 |
| SNP09979 | SEQ ID NO: 7 | T/C | 2030525 | 2030494 | 2030614 |
| NCSB_000550 | SEQ ID NO: 8 | A/G | 2042097 | 2042038 | 2042158 |
| SNP5610_Magellan | SEQ ID NO: 9 | A/G | 2095329 | 2095333 | 2095389 |
| SNP5617_Magellan | SEQ ID NO: 10 | A/G | 2134691 | 2134631 | 2134751 |
| NCSB_000551 | SEQ ID NO: 11 | T/C | 2161459 | 2161398 | 2161518 |
| SNP5631_Magellan | SEQ ID NO: 12 | T/C | 2194394 | 2194334 | 2194454 |
| NCSB_000552 | SEQ ID NO: 13 | A/G | 2239604 | 2239560 | 2239680 |
| BARC_044123_08621 | SEQ ID NO: 14 | C/G | — | 2277352 | 2278093 |
| NCSB_000553 | SEQ ID NO: 15 | A/T | 2322483 | 2322435 | 2322555 |
| NCSB_000554 | SEQ ID NO: 16 | A/G | 2414989 | 2414939 | 2415059 |
| Gmax7x162_1365688 | SEQ ID NO: 17 | A/G | — | 2457747 | 2457867 |
| NCSB_000555 | SEQ ID NO: 18 | A/G | 2483210 | 2483173 | 2483293 |
| Gmax7x162_1451621 | SEQ ID NO: 19 | A/T | — | 2543138 | 2543258 |
| NCSB_000556 | SEQ ID NO: 20 | T/C | 2551406 | 2551360 | 2551480 |
| BARC_051877_11277 | SEQ ID NO: 21 | C/G | — | 2555405 | 2555766 |
| BARC_051877_11280 | SEQ ID NO: 22 | A/G | — | 2555405 | 2555766 |
| SNP13346 | SEQ ID NO: 23 | T/G | 2735461 | 2735393 | 2735513 |
| BARC_027728_06650_1 | SEQ ID NO: 24 | A/G | — | 2740834 | 2741494 |
| BARC_027728_06650_2 | SEQ ID NO: 25 | T/C | — | 2740834 | 2741494 |
| NCSB_000557 | SEQ ID NO: 26 | T/C | 2746959 | 2746900 | 2747020 |
| BARC_030965_06980 | SEQ ID NO: 27 | T/C | — | 2785339 | 2785890 |
| NCSB_000558 | SEQ ID NO: 28 | C/G | 2827042 | 2826974 | 2827094 |
| NCSB_000559 | SEQ ID NO: 29 | A/T | 2904801 | 2904738 | 2904858 |
| Gmax7x198_656813 | SEQ ID NO: 30 | A/T | — | 2907997 | 2908117 |
| SNP3510_PI516C | SEQ ID NO: 31 | T/C | 2915547 | 2915487 | 2915607 |
| BARC_041781_08094_1 | SEQ ID NO: 32 | T/C | — | 2933490 | 2933794 |
| BARC_041781_08094_2 | SEQ ID NO: 33 | A/T | — | 2933490 | 2933794 |
| BARC_041781_08098 | SEQ ID NO: 34 | T/C | — | 2933541 | 2933792 |

TABLE 3-continued

List of the 115 SNP markers screened on the marker screening panel.

| Marker Name | Sequence | SNP | Position (bp) | Start (bp) | End (bp) |
|---|---|---|---|---|---|
| NCSB_000560 | SEQ ID NO: 35 | A/C | 2979605 | 2979546 | 2979666 |
| BARC_028645_05979 | SEQ ID NO: 36 | T/C | — | 2993383 | 2993935 |
| NCSB_000561 | SEQ ID NO: 37 | A/T | 3003271 | 3003212 | 3003332 |
| BARC_056039_14002 | SEQ ID NO: 38 | T/C | — | 3017671 | 3018282 |
| BARC_056115_14110 | SEQ ID NO: 39 | T/G | — | 3017714 | 3018262 |
| NCSB_000562 | SEQ ID NO: 40 | A/C | 3045691 | 3045608 | 3045728 |
| NCSB_000563 | SEQ ID NO: 41 | A/T | 3084032 | 3083955 | 3084075 |
| SNP5728_Magellan | SEQ ID NO: 42 | T/C | 3096381 | 3096321 | 3096441 |
| NCSB_001474 | SEQ ID NO: 43 | A/T | — | 3106436 | 3106554 |
| NCSB_000564 | SEQ ID NO: 44 | A/C | 3132867 | 3132793 | 3132913 |
| BARC_013815_01247 | SEQ ID NO: 45 | A/T | — | 3170167 | 3170706 |
| NCSB_000565 | SEQ ID NO: 46 | T/C | 3176950 | 3176891 | 3177011 |
| SNP13277 | SEQ ID NO: 47 | A/G | 3237646 | 3237579 | 3237699 |
| NCSB_000566 | SEQ ID NO: 48 | A/T | 3261666 | 3261607 | 3261727 |
| BARC_028619_05977 | SEQ ID NO: 49 | A/G | — | 3298954 | 3299498 |
| NCSB_000567 | SEQ ID NO: 50 | T/C | 3313385 | 3313274 | 3313440 |
| Gmax7x198_230985 | SEQ ID NO: 51 | A/C | — | 3333673 | 3333793 |
| NCSB_000568 | SEQ ID NO: 52 | A/T | 3341379 | 3341317 | 3341437 |
| Gmax7x198_174690 | SEQ ID NO: 53 | A/G | — | 3390392 | 3390512 |
| NCSB_000569 | SEQ ID NO: 54 | T/C | 3394116 | 3394056 | 3394149 |
| NCSB_000570 | SEQ ID NO: 55 | A/T | 3463883 | 3463823 | 3463943 |
| NCSB_000571 | SEQ ID NO: 56 | T/C | 3518009 | 3517924 | 3518044 |
| NCSB_000572 | SEQ ID NO: 57 | T/G | 3539955 | 3539896 | 3540016 |
| NCSB_000573 | SEQ ID NO: 58 | A/G | 3593983 | 3593905 | 3594025 |
| NCSB_000574 | SEQ ID NO: 59 | T/G | 3626800 | 3626734 | 3626854 |
| NCSB_000575 | SEQ ID NO: 60 | T/C | 3669543 | 3669465 | 3669585 |
| NCSB_000576 | SEQ ID NO: 61 | A/C | 3774187 | 3774117 | 3774237 |
| BARC_027438_06568 | SEQ ID NO: 62 | T/C | — | 3805216 | 3805783 |
| BARC_064351_18627 | SEQ ID NO: 63 | T/C | — | 3826881 | 3827418 |
| BARC_064351_18628 | SEQ ID NO: 64 | A/G | — | 3826881 | 3827418 |
| BARC_064351_18629 | SEQ ID NO: 65 | T/C | — | 3826881 | 3827418 |
| BARC_064351_18630 | SEQ ID NO: 66 | T/C | — | 3826881 | 3827418 |
| BARC_064351_18631 | SEQ ID NO: 67 | T/C | — | 3826881 | 3827418 |
| SNP18196 | SEQ ID NO: 68 | A/G | 3843479 | 3843406 | 3843526 |
| NCSB_000577 | SEQ ID NO: 69 | T/G | 3862087 | 3862027 | 3862147 |
| NCSB_000174 | SEQ ID NO: 70 | T/C | — | 3865826 | 3865918 |
| SNP5855_Magellan | SEQ ID NO: 71 | A/G | 3874278 | 3874218 | 3874309 |
| Gmax7x259_98606 | SEQ ID NO: 72 | A/C | — | 3889538 | 3889658 |
| BARC_005095_00281 | SEQ ID NO: 73 | A/G | — | 3910266 | 3910317 |
| SNP18188 | SEQ ID NO: 74 | T/G | 3915285 | 3915214 | 3915334 |
| NCSB_000578 | SEQ ID NO: 75 | T/G | — | 3927664 | 3927784 |
| Gmax7x259_53391 | SEQ ID NO: 76 | A/T | — | 3934846 | 3934966 |
| Gmax7x259_44054 | SEQ ID NO: 77 | A/C | — | 3944185 | 3944305 |
| NCSB_000579 | SEQ ID NO: 78 | T/C | 3953122 | 3953050 | 3953170 |
| BARC_014709_01624 | SEQ ID NO: 79 | A/C | — | 3963476 | 3964684 |
| BARC_014709_01625 | SEQ ID NO: 80 | A/G | — | 3963476 | 3964684 |
| BARC_014709_01626 | SEQ ID NO: 81 | T/C | — | 3963476 | 3964684 |
| BARC_014709_01628 | SEQ ID NO: 82 | T/C | — | 3963476 | 3964684 |
| BARC_014709_01629 | SEQ ID NO: 83 | T/G | — | 3963476 | 3964684 |
| BARC_014709_01630 | SEQ ID NO: 84 | T/C | — | 3963476 | 3964684 |
| BARC_014709_01631 | SEQ ID NO: 85 | A/G | — | 3963476 | 3964684 |
| Gmax7x259_17365 | SEQ ID NO: 86 | A/G | — | 3970867 | 3970987 |
| BARC_051499_11144 | SEQ ID NO: 87 | T/C | 4038123 | 4038071 | 4038430 |
| BARC_051499_11145 | SEQ ID NO: 88 | C/G | 4038339 | 4038071 | 4038430 |
| BARC_064081_18547 | SEQ ID NO: 89 | A/G | — | 4062560 | 4062876 |
| NCSB_000160 | SEQ ID NO: 90 | T/C | — | 4183691 | 4183762 |
| NCSB_000580 | SEQ ID NO: 91 | A/T | 4198334 | 4198261 | 4198306 |
| BARC_060517_16709 | SEQ ID NO: 92 | A/G | — | 4309301 | 4309694 |
| NCSB_000582 | SEQ ID NO: 93 | A/G | — | 4547450 | 4547570 |
| BARC_058135_15105 | SEQ ID NO: 94 | T/C | — | 4551023 | 4551077 |
| BARC_058135_15106 | SEQ ID NO: 95 | C/G | — | 4551023 | 4551077 |
| BARC_058135_15107 | SEQ ID NO: 96 | T/G | — | 4551023 | 4551077 |
| BARC_058135_15108 | SEQ ID NO: 97 | A/G | — | 4551023 | 4551077 |
| BARC_058135_15109 | SEQ ID NO: 98 | T/C | — | 4551023 | 4551077 |
| BARC_058135_15110 | SEQ ID NO: 99 | T/G | — | 4551023 | 4551077 |
| NCSB_000583 | SEQ ID NO: 100 | A/C | 4602406 | 4602328 | 4602448 |
| NCSB_000584 | SEQ ID NO: 101 | T/C | 4649955 | 4648129 | 4650001 |
| BARC_043191_08550 | SEQ ID NO: 102 | T/C | — | 4688339 | 4688641 |
| BARC_043191_08551 | SEQ ID NO: 103 | A/G | — | 4688339 | 4688641 |
| SNP5970_Magellan | SEQ ID NO: 104 | A/C | 4694539 | 4694389 | 4694559 |
| NCSB_000585 | SEQ ID NO: 105 | T/C | 4738427 | 4738342 | 4738462 |
| NCSB_000586 | SEQ ID NO: 106 | A/G | 4775267 | 4775207 | 4775327 |
| BARC_057997_15049 | SEQ ID NO: 107 | A/G | — | 4810812 | 4811005 |
| BARC_057997_15050 | SEQ ID NO: 108 | T/C | — | 4810812 | 4811005 |
| NCSB_000587 | SEQ ID NO: 109 | A/G | 4831681 | 4831609 | 4831727 |
| SNP5996_Magellan | SEQ ID NO: 110 | A/C | 4837292 | 4837232 | 4837347 |

TABLE 3-continued

List of the 115 SNP markers screened on the marker screening panel.

| Marker Name | Sequence | SNP | Position (bp) | Start (bp) | End (bp) |
|---|---|---|---|---|---|
| NCSB_000588 | SEQ ID NO: 111 | T/C | 4894872 | 4894798 | 4894918 |
| BARC_044085_08610_1 | SEQ ID NO: 112 | T/C | — | 8157986 | 8158595 |
| BARC_044085_08610_2 | SEQ ID NO: 113 | A/G | — | 8157986 | 8158595 |
| BARC_044085_08610_3 | SEQ ID NO: 114 | T/C | — | 8157986 | 8158595 |
| BARC_046750_12729 | SEQ ID NO: 115 | A/G | — | 9061972 | 9062248 |

Example 7: Mapping and Statistical Analysis

Pearson's Chi-squared test was used to analyze the association between the 24 SNP markers described in Table 2 and the Rps1-k resistance phenotype. JMP® 9.0 (SAS, Cary, N.C.) was used for all Chi-squared analysis. As a result of the statistical analysis of the data from the 3 mapping populations, 10 of the 24 markers were determined to be tightly linked with Rps1-k specific *phytophthora* resistance and produced p-values less than 0.0001. These 10 tightly linked markers are shown in Table 4A and the KASPar™ assay primer sequences are described in Table 4B. All 10 markers were polymorphic in the Rps1-k×Rps1-c soybean line mapping population and 5 were polymorphic in the Rps1-k soybean line population. The sample segregation ratio (AA:AB:BB) in the Rps1-k×Rps1-c mapping population was roughly 1:2:1 for the 10 SNPs. The Chi-squared association test data are show in Table 5 for the Rps1-k× Rps1-c mapping population and in Table 6 for the Rps1-k mapping population.

There are several explanations for the low $R^2$ values shown in Tables 5 and 6. The Rps1-k gene(s) are a class of highly clustered R genes encoding coiled coil-nucleotide binding site leucine-rich repeat (CC-NBS-LRR) proteins (Gao et al. 2005). The soybean genome is estimated to contain about 38 copies of similar Rps1-k gene sequences, most of which are clustered in approximately 600 kb of contiguous DNA of the Rps1-k region (Bhattacharyya et al. 2005). The identification of unique and specific nucleotide sequences for designing primers and probes from such a high number of gene copies within this gene family is challenging. The lack of readily identifiable gene-specific markers may explain the low $R^2$ values.

In addition, it is possible that Rps1-k resistance is caused by other Rps QTLs in addition to the Rps1-k gene. Partial resistance to *phytophthora* that is not gene-specific has been reported in many publications (Burnham et al. 2003; Ferro et al. 2006; Li et al. 2010; Ranathunge et al. 2008; Tucker et al. 2010). Currently, the phenotyping process cannot separate partial resistance from gene-specific resistance. The phenotypic complexity of this disease and the multiple copies of highly similar gene sequences make marker development more elusive and highly challenging.

Figure 3:
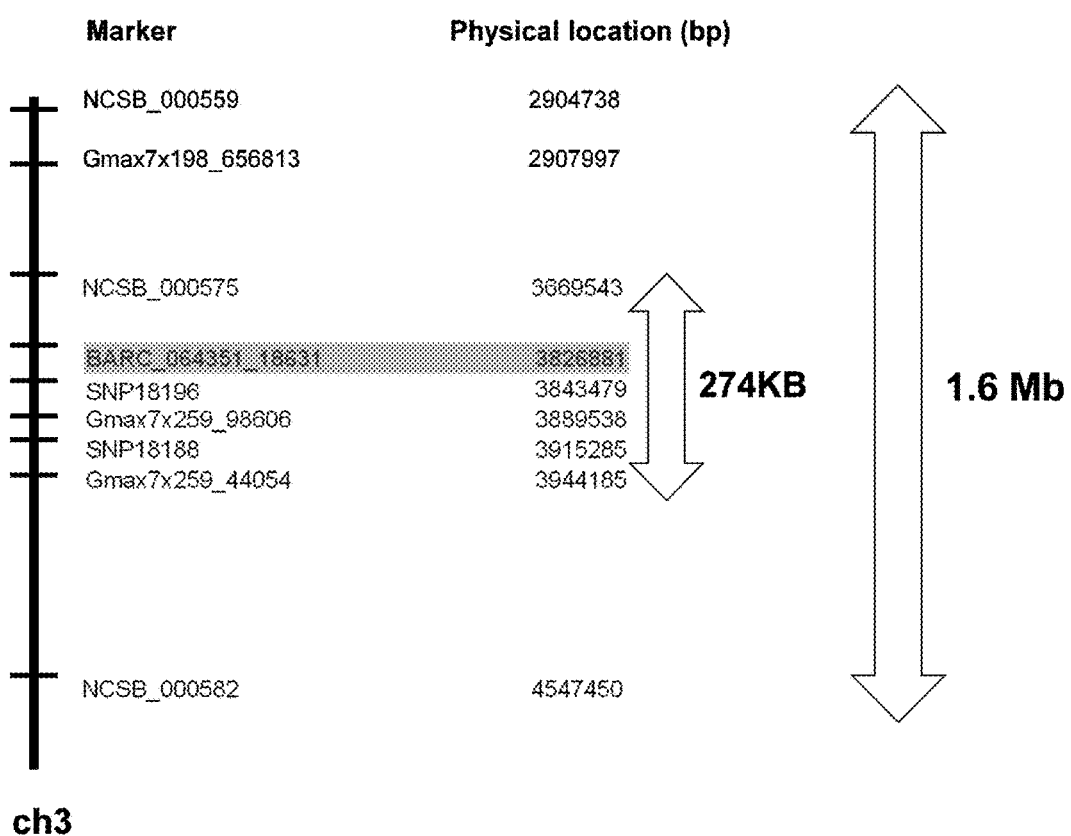
FIG. 3 includes the physical map of polymorphic SNPs markers identified on chromosome 3. BARC_064351_18628 was located roughly at the same locus as BARC_064351_18631.

JoinMap® 4.0 (Van Ooijen, 2006) was used to construct a linkage group (LG) to confirm that the markers were mapped with the *phytophthora* phenotypic trait together on LG N of chromosome 3. QTL analysis was carried out using JMP® Genomics 5.0 (SAS, Cary, N.C.). QTL analysis confirmed that all the polymorphic SNPs were mapped together with Rps1-k phenotypic resistance on the same linkage group (FIG. 3).

TABLE 4

Summary of the 10 SNP markers that are used for identification of *phytophthora* resistant soybean lines and their KASPAR™ primer sequences.

Table 4A:

| SNP Marker | SNP | Sequence of SNP Marker Comprising *Phytophthora* Resistance | Physical Location on Chromosome 3 | Polymorphism Present in Breeding Population |
|---|---|---|---|---|
| Gmax7 × 198_656813 | A/T at bp 61 | SEQ ID NO: 151 | 2,904,738 to 2,904,858 | 1-k × 1-c |
| NCSB_000559 | A/T at bp 61 | SEQ ID NO: 150 | 2,907,997 to 2,908,117 | 1-k × 1-c |
| SNP18196 | A/G at bp 61 | SEQ ID NO: 152 | 3,843,406 to 3,843,526 | 1-k × 1-c and 1-k |
| NCSB_000575 | T/C at bp 61 | SEQ ID NO: 153 | 3,669,465 to 3,669,585 | 1-k × 1-c |
| Gmax7 × 259_44054 | A/C at bp 61 | SEQ ID NO: 154 | 3,994,185 to 3,994,305 | 1-k × 1-c and 1-k |
| SNP18188 | T/G at bp 61 | SEQ ID NO: 155 | 3,915,214 to 3,915,334 | 1-k × 1-c |
| Gmax7 × 259_98606 | A/G at bp 61 | SEQ ID NO: 156 | 3,889,538 to 3,889,658 | 1-k × 1-c |
| BARC_064351_18628 | A/G at bp 95 | SEQ ID NO: 157 | 3,826,881 to 3,827,418 | 1-k × 1-c and 1-k |
| BARC_064351_18631 | T/C at bp 73 | SEQ ID NO: 158 | 3,826,881 to 3,827,418 | 1-k × 1-c and 1-k |
| NCSB_000582 | A/G at bp 61 | SEQ ID NO: 159 | 4,547,450 to 4,547,570 | 1-k × 1-c and 1-k |

TABLE 4-continued

Summary of the 10 SNP markers that are used for identification of *phytophthora* resistant soybean lines and their KASPAR ™ primer sequences.

Table 4B:

| Primer | Sequence |
|---|---|
| Gmax7 x 198_656813_A1 | SEQ ID NO: 116 |
| Gmax7 x 198_656813_A2 | SEQ ID NO: 117 |
| Gmax7 x 198_656813_C1 | SEQ ID NO: 118 |
| NCSB_000559_A1 | SEQ ID NO: 119 |
| NCSB_000559_A2 | SEQ ID NO: 120 |
| NCSB_000559_C1 | SEQ ID NO: 121 |
| SNP18196_A1 | SEQ ID NO: 122 |
| SNP18196_A2 | SEQ ID NO: 123 |
| SNP18196_C1 | SEQ ID NO: 124 |
| NCSB_000575_A1 | SEQ ID NO: 125 |
| NCSB_000575_A2 | SEQ ID NO: 126 |
| NCSB_000575_C1 | SEQ ID NO: 127 |
| Gmax7 x 259_44054_A1 | SEQ ID NO: 128 |
| Gmax7 x 259_44054_A2 | SEQ ID NO: 129 |
| Gmax7 x 259_44054_C1 | SEQ ID NO: 130 |
| SNP18188_A1 | SEQ ID NO: 131 |
| SNP18188_A2 | SEQ ID NO: 132 |
| SNP18188_C1 | SEQ ID NO: 133 |
| Gmax7 x 259_98606_A1 | SEQ ID NO: 134 |
| Gmax7 x 259_98606_A2 | SEQ ID NO: 135 |
| Gmax7 x 259_98606_C1 | SEQ ID NO: 136 |
| BARC_064351_18628_A1 | SEQ ID NO: 137 |
| BARC_064351_18628_A2 | SEQ ID NO: 138 |
| BARC_064351_18628_C1 | SEQ ID NO: 139 |
| BARC_064351_18631_A1 | SEQ ID NO: 140 |
| BARC_064351_18631_A2 | SEQ ID NO: 141 |
| BARC_064351_18631_C1 | SEQ ID NO: 142 |
| NCSB_000582_A1 | SEQ ID NO: 143 |
| NCSB_000582_A2 | SEQ ID NO: 144 |
| NCSB_000582_C1 | SEQ ID NO: 145 |

TABLE 5

The association tests of the 10 SNP genotypes with the Rps1-k resistant phenotypes in the Rps1-k x Rps1-c mapping population ($p < 0.0001$).

| Marker | Chromosome | Resistant Genotype | Chi-squared | % Variance Explained ($R^2$) | LOD |
|---|---|---|---|---|---|
| Gmax7 x 198_656813 | 3 | T:T | 155.32 | 34.97 | 71.08 |
| NCSB_000559 | 3 | T:T | 168.46 | 37.47 | 77.75 |
| SNP18196 | 3 | G:G | 149.32 | 51 | 76.46 |
| NCSB_000575 | 3 | C:C | 193.9 | 43.19 | 87.61 |
| Gmax7 x 259_44054 | 3 | C:C | 198.28 | 43.86 | 89.4 |
| SNP18188 | 3 | T:T | 216.48 | 49.51 | 98.91 |
| Gmax7 x 259_98606 | 3 | A:A | 203.62 | 43.91 | 93.47 |
| BARC_064351_18628 | 3 | G:G | 134.26 | 47.94 | 65.12 |
| BARC_064351_18631 | 3 | C:C | 196.44 | 45.33 | 87.77 |
| NCSB_000582 | 3 | G:G | 200.18 | 44.33 | 91.14 |

TABLE 6

The association tests of the identified 5 polymorphic SNP genotypes with the Rps1-k resistant phenotypes in the Rps1-k mapping population ($p < 0.0001$).

| Marker | Chromosome | Resistant Genotype | Chi-squared | % Variance Explained ($R^2$) | LOD |
|---|---|---|---|---|---|
| SNP18196 | 3 | G:G | 78.133 | 25.31 | 33.84 |
| Gmax7 x 259_44054 | 3 | C:C | 81.87 | 27.87 | 36.08 |
| BARC_064351_18628 | 3 | G:G | 75.19 | 23.38 | 32.8 |
| BARC_064351_18631 | 3 | C:C | 77.93 | 27.2 | 35.96 |
| NCSB_000582 | 3 | G:G | 84.66 | 28.49 | 36.56 |

The disclosure of the ten SNP markers that are tightly linked with soybean *phytophthora* resistance trait, Rps1-k, provide reagents which can be utilized for the mapping of *phytophthora* resistance in soybean lines. The ten SNP markers were identified out of 115 SNP markers using a KASPAR™ genotyping platform. The ten SNP markers that were identified were isolated and can now be utilized to screen soybean populations for *phytophthora* resistance, and the zygosity of soybean plants for the *phytophthora* QTL. All ten of the SNP markers were mapped on chromosome 3 to linkage group N. The ten SNP markers comprise a contiguous chromosomal fragment which contains QTL for *phytophthora* resistance. The contiguous chromosomal fragment spans a fragment comprising base pair 2,904,738 to 4,547,450 on chromosome 3 as is illustrated in FIG. 3.

Example 8: Plant Material and DNA Extraction

The Rps1-k TAQMAN™ assay was validated using a soybean breeding population, consisting of 359 lines that were segregating for Rps1-k resistance. Genomic DNA from the soybean lines was isolated from 1 leaf disc per sample using the MAGATTRACT™ DNA extraction kit (Qiagen, Valencia, Calif.) per manufacturer's instructions.

Example 9: Endpoint TAQMAN™ Assay Development

The endpoint TAQMAN™ assay was developed for the detection of *phytophthora* locus Rps1-k resistance and is based on the sequence of a tightly linked Single Nucleotide Polymorphism (SNP) marker. The SNP marker, BARC_064351_18631 (SEQ ID NO: 158), was identified as linked to the Rps1-k locus on linkage group N and features a T:C SNP. The presence of the T allele indicates that soybean plants are susceptible to *phytophthora* infestation, while the presence of the C allele indicates that soybean plants are resistant to *phytophthora* infestation. The Rps1-k TAQMAN™ assay resulted in the amplification of a 72-bp fragment using the common forward primer, D-Sb-Rps1k-F, and common reverse primer, D-Sb-Rps1k-R. The oligonucleotide probe specific to the resistant allele (D-Sb-Rps1k-FM) and that of the susceptible allele (D-Sb-Rps1k-VC) bind to the amplicon between the two primers and are labeled with the FAM and VIC fluorescent reporter dyes, respectively, at the 5' end and MGBNFQ (minor grove binding non-fluorescent quencher) as a quencher at the 3' end. PCR products are measured using a spectrofluorometer at the end of the thermocycling program. Genotype is determined by the presence or absence of fluorescence specific to either the resistant allele or the susceptible allele. Common primers and allele specific probes were designed using Applied Biosystem's Custom Design service (Foster City, Calif.). Primer and probe sequences are listed in Table 7.

TABLE 7

List of primers and probes for Rps1-k TAQMAN ™ endpoint assay.

| Name | Function | Sequence | SEQ ID |
|---|---|---|---|
| D-Sb-Rps1k-F | forward primer | TGAAGCTGCTAAACCACCA GAAT | 146 |
| D-Sb-Rps1k-R | reverse primer | AATTGCTAAGGTCAATCAC TGAATATTGGA | 147 |
| D-Sb-Rps1k-FM | resistant probe | ATTCCCATAGCTCCCG | 148 |
| D-Sb-Rps1k-VC | susceptible probe | CATTCCCATAACTCCCG | 149 |

Example 10: PCR Conditions and Analysis

Components for a TAQMAN™ reaction containing oligonucleotides specific for Rps1-k genomic sequence are shown in Table 8. The PCR reaction mixture was prepared as a Master Mix containing all components except the DNA templates. The PCR reaction mix was dispensed into a 384-well plate (Abgene, Rochester, N.Y.). Genomic DNA templates and positive and negative controls, shown in Table 9, were then included in separate wells of the plate. The reactions was amplified in a GENAMP PCR SYSTEM 9700™ (Applied Biosystems, Foster City, Calif.) under the following cycling conditions: 1 cycle at 50° C. for 2 minutes; 1 cycle at 95° C. for 10 minutes; and 35 cycles at 95° C. for 15 seconds and 60° C. for 30 seconds. Following completion of the TAQMAN™ PCR and fluorescence reading reactions, a distribution graph was generated.

Example 11: Validation of the Rps1-k TAQMAN™ Assay

Figure 4:
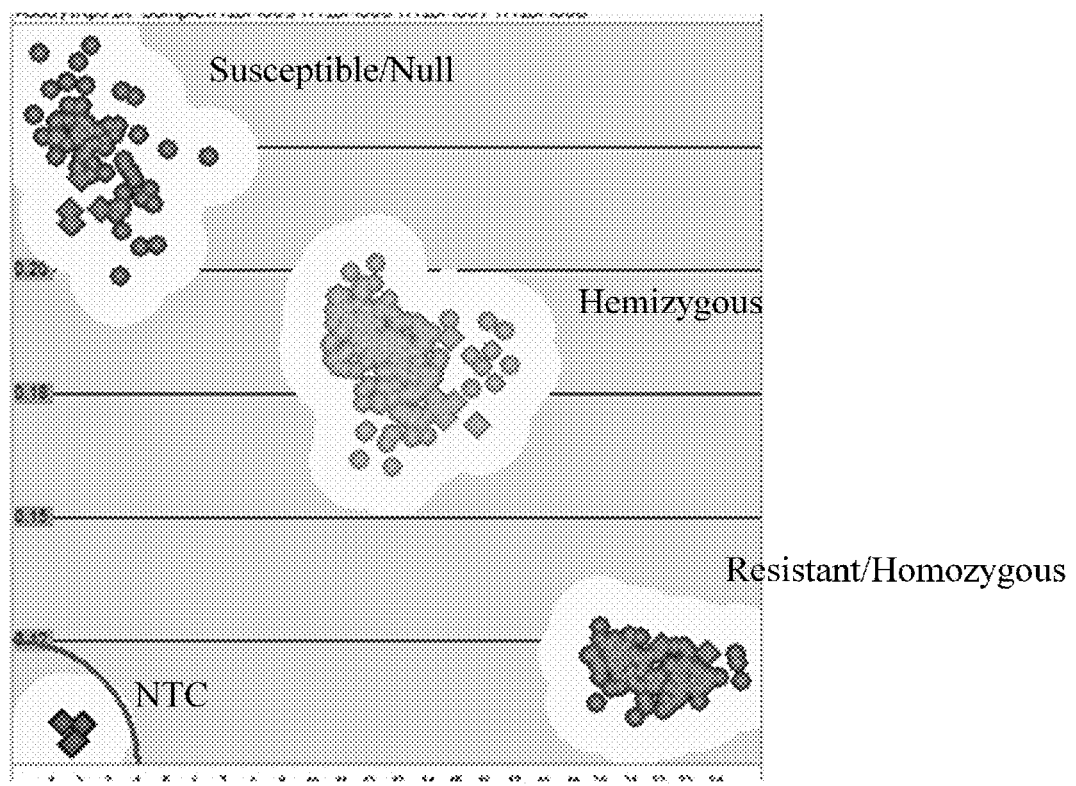
FIG. 4 describes a distribution graph, based on Relative Fluorescence Units (RFU), of the Rps1-k TAQMAN™ specific assay developed from the SNP marker, BARC_064351_18631.

The TAQMAN™ assay was validated using a soybean breeding population of 359 lines which were segregating for *phytophthora* resistance (FIG. 4). Homozygous samples containing the Rps1-k susceptible allele resulted in Relative Fluorescence Units (RFU) readings of the VIC dye only. These samples are shown in the upper left hand cluster and have a genotype of T:T. Heterozygous samples which contain one copy of the Rps1-k susceptible allele and a second copy of the Rps1-k resistant allele are shown in the upper right hand cluster and have a genotype of T:C. Homozygous samples containing the Rps1-k resistant allele are shown in the lower right cluster and have a genotype of C:C. Samples that were heterozygous or homozygous for the Rps1-k resistant allele resulted in Relative Fluorescence Units (RFU) readings for the FAM dye at least 0.5-1 unit higher than that of the no template control (NTC), which is shown in the lower left hand corner.

Genotypic calls for the population were compared with those of alternative gel-based PCR assay and the phenotypic scores which were determined from susceptibility or resistance to *phytophthora* infestation. The genotypes based on the TAQMAN™ assay of the breeding population corresponded with the genotypes based on the alternative gel-based PCR assay (only one sample of the 354 lines showed a discrepancy between the alternative gel-based PCR method and the novel TAQMAN™ assay).

TABLE 8

PCR mix for Rps1-k TAQMANT ™ assay

| Component | Stock Concentration | Final Volume (μl) |
|---|---|---|
| TAQMAN ™ Genotyping Master Mix | 2X | 2.0 |
| D-Sb-Rps1k-F | 20 μM | 0.1 |
| D-Sb-Rps1k-R | 20 μM | 0.1 |
| D-Sb-Rps1k-VC | 10 μM | 0.1 |
| D-Sb-Rps1k-FM | 10 μM | 0.1 |
| 0.8% Polyvinylpyrrolidone (PVP) | — | 0.6 |
| Sample DNA | — | 1.0 |
| Total volume | — | 4.0 |

TABLE 9

Positive and negative controls for Rps1-k assay.

| Type of Control | Description | Expected Result | Interpretation |
|---|---|---|---|
| Master mix negative control | No DNA is added to the reaction. | Background RFU readings. No PCR products. | Mix is not contaminated. |
| Mut/Resistant DNA positive control | Genomic DNA sample known to be homozygous for the Rps1-k resistance is added. | The FAM fluorescent signal is the only signal observed. No VIC signal present. | Control shows amplification of the resistance allele (FAM) and no amplification from the susceptible (VIC) allele from genomic DNA. |

TABLE 9-continued

Positive and negative controls for Rps1-k assay.

| Type of Control | Description | Expected Result | Interpretation |
|---|---|---|---|
| Heterozygous DNA positive control | Genomic DNA sample known to be heterozygous for the Rps1-k resistance is added. | The FAM and VIC signal are both present at equal units. | Control shows amplification of the resistant allele (FAM) and the susceptible allele (VIC) from genomic DNA. |
| Wildtype/ Conventional DNA negative control | Genomic DNA sample known to be homozygous for the Rps1-k susceptibility is added. | The VIC fluorescent signal is the only signal observed. No FAM signal present. | Control only shows amplification of the susceptible allele (VIC) and no amplification of the resistant allele (FAM) from genomic DNA. |

The TAQMAN® detection method for *phytophthora* resistance in soybean was tested against 354 soybean lines which comprise *phytophthora* resistant and *phytophthora* susceptible phenotypes. The assay was successfully designed to specifically detect the soybean SNP marker BARC_064351_18631 (SEQ ID NO: 158) which identifies soybean plants that are resistant to *phytophthora*. The event specific primers and probes can be used effectively for the detection of the soybean SNP marker BARC_064351_18631 (SEQ ID NO:158) and these conditions and reagents are applicable for zygosity assays.

Finally, the skilled artisan would appreciate that the TAQMAN® method described in the preceding examples is readily applicable for the detection of the other soybean SNP markers, described within this disclosure, which can be used to identify soybean plants that are resistant to *phytophthora* resistance. For example, the SNP markers of Table 4A provide sequences that can be used for the design of primers and probes which can be specifically used to detect the SNP marker via a TAQMAN® assay. In addition, the TAQMAN® assay conditions may be modified by altering the reagent components, and changing the amplification temperatures and conditions. The skilled artisan would understand that the teachings of this disclosure provide guidance to design such TAQMAN® assays for the detection of any SNP markers disclosed herein. For example; TAQMAN® assays for the detection of the *phytophthora* resistance SNP markers of Gmax7x198_656813 (SEQ ID NO:151), NCSB_000559 (SEQ ID NO:150), SNP18196 (SEQ ID NO:152), NCSB_000575 (SEQ ID NO:153), Gmax7x 259_44054 (SEQ ID NO:154), SNP18188 (SEQ ID NO:155), Gmax7x259_98606 (SEQ ID NO:156), BARC_064351_18628 (SEQ ID NO:157), and NCSB_000582 (SEQ ID NO: 159) are within the scope of the current disclosure.

While aspects of this invention have been described in certain embodiments, they can be further modified within the spirit and scope of this disclosure. This application is therefore intended to cover any variations, uses, or adaptations of embodiments of the invention using its general principles. Further, this application is intended to cover such departures from the present disclosure as come within known or customary practice in the art to which these embodiments pertain and which fall within the limits of the appended claims.

What is claimed is:

1. A method for producing a *phytophthora*-resistant soybean plant, the method comprising:
   amplifying a genomic polynucleotide from a first soybean plant by performing a polymerase chain reaction (PCR), wherein the genomic polynucleotide comprises SEQ ID NO:67;
   contacting the genomic polynucleotide with a detectable oligonucleotide probe that specifically hybridizes to the single nucleotide polymorphism (SNP) allele of a C residue at position 11 of SEQ ID NO:67;
   detecting a signal confirming hybridization of the detectable oligonucleotide probe to the genomic polynucleotide;
   crossing the first soybean plant with a second, *phytophthora*-susceptible soybean plant that does not comprise the SNP allele of a C residue at position 11 of SEQ ID NO:67 in its genome, thereby producing $F_1$ progeny plants; and
   growing an $F_1$ progeny plant that comprises the SNP allele of a C residue at position 11 of SEQ ID NO:67 in its genome.

2. The method according to claim 1, wherein the PCR is a competitive allele-specific polymerase chain reaction.

3. The method according to claim 1, wherein the genomic polynucleotide is amplified from the isolated nucleic acid molecules utilizing at least primer oligonucleotide selected from the group consisting of SEQ ID NO: 140 and SEQ ID NO:141.

4. The method according to claim 1, the method further comprising:
   backcrossing the $F_1$ progeny plant that comprises the SNP allele of a C residue at position 11 of SEQ ID NO:67 in its genome with the first or second soybean plant, to produce further progeny plants; and
   growing a further progeny plant that comprises the SNP allele of a C residue at position 11 of SEQ ID NO:67 in its genome.

5. The method according to claim 4, wherein the SNP allele of a C residue at position 11 of SEQ ID NO:67 is identified in the further progeny plant by a competitive allele-specific polymerase chain reaction.

* * * * *